(12) United States Patent
Fujihara et al.

(10) Patent No.: US 11,311,013 B2
(45) Date of Patent: Apr. 26, 2022

(54) BENZIMIDAZOLE COMPOUND OR SALT THEREOF, AGRICULTURAL AND HORTICULTURAL INSECTICIDAL AND ACARICIDAL AGENT CONTAINING SAID COMPOUND, AND METHOD FOR USING SAME

(71) Applicant: NIHON NOHYAKU CO., LTD., Tokyo (JP)

(72) Inventors: Hirokazu Fujihara, Kawachinagano (JP); Yutaka Abe, Kawachinagano (JP); Ryosuke Tanaka, Kawachinagano (JP); Shunsuke Fuchi, Kawachinagano (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 0 days.

(21) Appl. No.: 17/057,563

(22) PCT Filed: May 22, 2019

(86) PCT No.: PCT/JP2019/020325
§ 371 (c)(1),
(2) Date: Nov. 20, 2020

(87) PCT Pub. No.: WO2019/225663
PCT Pub. Date: Nov. 28, 2019

(65) Prior Publication Data
US 2021/0204545 A1     Jul. 8, 2021

(30) Foreign Application Priority Data

May 22, 2018 (JP) .............................. JP2018-097629

(51) Int. Cl.
*A01N 43/52* (2006.01)
*A61P 33/10* (2006.01)
*C07D 401/04* (2006.01)

(52) U.S. Cl.
CPC .............. *A01N 43/52* (2013.01); *A61P 33/10* (2018.01); *C07D 401/04* (2013.01)

(58) Field of Classification Search
CPC ........ A01N 43/52; A61P 33/10; C07D 401/14
See application file for complete search history.

(56) References Cited

U.S. PATENT DOCUMENTS

| | | | |
|---|---|---|---|
| 8,853,238 B2 | 10/2014 | Takyo et al. | |
| 9,018,134 B2 | 4/2015 | Takahashi et al. | |
| 9,120,823 B2 | 9/2015 | Takahashi | |
| 9,278,983 B2 | 3/2016 | Takyo et al. | |
| 9,353,110 B2 | 5/2016 | Takahashi et al. | |
| 9,403,771 B2 | 8/2016 | Takahashi et al. | |
| 9,936,703 B2 * | 4/2018 | Yonemura ............ | C07D 487/04 |
| 2014/0018373 A1 | 1/2014 | Takyo et al. | |
| 2014/0364444 A1 | 12/2014 | Takyo et al. | |
| 2015/0197532 A1 | 7/2015 | Takahashi et al. | |
| 2016/0009715 A1 | 1/2016 | Takahashi et al. | |
| 2016/0159743 A1 | 6/2016 | Takahashi et al. | |
| 2017/0210741 A1 | 7/2017 | Augelli-Szafran et al. | |

FOREIGN PATENT DOCUMENTS

| | | |
|---|---|---|
| WO | WO 2008/128968 A1 | 10/2008 |
| WO | WO 2009/051705 A1 | 4/2009 |
| WO | WO 2012/086848 A1 | 6/2012 |
| WO | WO 2013/018928 A1 | 2/2013 |

OTHER PUBLICATIONS

International Search Report dated Aug. 20, 2019, in PCT/JP2019/020325.
Maiti, S. and P. Mal, "Phenyliodine Diacetate-Mediated Intramolecular C(sp²)-H Amidation for 1,2-Disubstituted Benzimidazole Synthesis under Metal-Free Conditions," Adv. Synth. Catal. (2015), vol. 357, pp. 1416-1424.
Wang et al., "Ferrocenesulfonyl Benzimidazole Derivatives Synthesized under Microwave Irradiation and Their Crystal Structure and Antimicrobial Activity," Chinese Journal of Applied Chemistry (May 2007), vol. 24, No. 5, pp. 507-511 (with abstract).
Database Registry [Online], Chemical Abstracts Service, Columbus. Ohio, US: Nov. 11, 2005, Database accession No. 867299-25-0.
Database Registry [Online], Chemical Abstracts Service, Columbus, Ohio, US: Dec. 12, 2005, Database accession No. 869710-31-6.
Database Registry [Online], Chemical Abstracts Service, Columbus, Ohio, US: Feb. 18, 2014, Database accession No. 1547651-08-0.

(Continued)

*Primary Examiner* — Timothy R Rozof
(74) *Attorney, Agent, or Firm* — Birch, Stewart, Kolasch & Birch, LLP

(57) ABSTRACT

The present invention has an object to develop and provide a novel agricultural and horticultural insecticidal and acaricidal agent due to the factors such as serious damages caused by pests and the like and growing resistant pests against existing drugs in the crop production such as agriculture and horticulture.

The present invention provides an agricultural and horticultural insecticidal and acaricidal agent having as an active ingredient a benzimidazole compound represented by general formula (1)

[Formula 1]

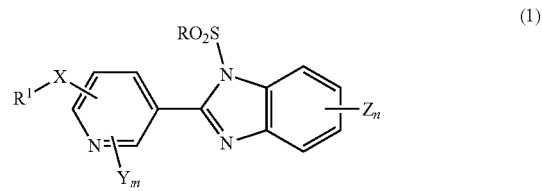

(1)

wherein R represents an alkyl group or the like, R¹ represents a haloalkyl group or the like, X represents an oxygen atom or the like, m and n represent 0 or the like, or a salt thereof, and a method for using the same.

10 Claims, No Drawings

(56) References Cited

OTHER PUBLICATIONS

European Search Report dated Feb. 18, 2022, in European Patent Application No. 19807201.9.
Savall, B. M. and Fontimayor, J. R., "Synthesis of 2-arylbenzimidazoles via microwave Suzuki-Miyura reaction of unprotected 2-chlorobenzimidazoles," Tetrahedron Letters (2008), vol. 49, pp. 6667-6669.

* cited by examiner

BENZIMIDAZOLE COMPOUND OR SALT THEREOF, AGRICULTURAL AND HORTICULTURAL INSECTICIDAL AND ACARICIDAL AGENT CONTAINING SAID COMPOUND, AND METHOD FOR USING SAME

TECHNICAL FIELD

The present invention relates to an agricultural and horticultural insecticidal and acaricidal agent having a benzimidazole compound or a salt thereof as an active ingredient and a method for using the same.

BACKGROUND ART

Benzimidazole compounds have been so far documented to be useful as an insecticidal agent (for example, see Patent Literatures 1 and 2); however, these literatures disclose no benzimidazole compound having a specific N-sulfonyl group such as an N-alkylsulfonyl group at position 1. These literatures disclose a benzimidazole compound wherein a pyridyl group binds to position 2 but provide no description regarding the compound having a specific N-sulfonyl group such as an alkylsulfonyl group at position 1 or an insecticidal effect (for example, see Non Patent Literatures 1 and 2).

CITATION LIST

Patent Literature

Patent Literature 1: International Publication No. WO2012/086848
Patent Literature 2: International Publication No. WO2013/018928

Non Patent Literature

Non Patent Literature 1: Advanced Synthesis & Catalysis (2015), 357(7), 1416-1424
Non Patent Literature 2: Yingyong Huaxue (2007), 24(5), 507-511

SUMMARY OF INVENTION

Technical Problem

In crop production in the fields of agriculture, horticulture and the like, damages caused by pests and the like have been still serious, and there is a demand for developing an agricultural and horticultural insecticidal and acaricidal agent having a novel action, less impact on natural enemy useful insects, and imparted with penetration and translocation activity, from the viewpoints of emergence of resistant pests against existing drugs, impacts on environmental biology and labor saving of operation.

Solution to Problem

The present inventors conducted extensive studies to solve the above problem and found that a benzimidazole compound represented by general formula (1) wherein a pyridyl group binds at position 2 and a specific N-sulfonyl group is present at position 1 or a salt thereof demonstrates not only a good controlling effect on agricultural and horticultural pests but can solve the above problem, whereby the present invention has been accomplished.

That is, the present invention relates to
[1] A benzimidazole compound represented by general formula (1)

[Formula 1]

(1)

wherein, R represents (a1) a $(C_1-C_8)$ alkyl group; (a2) a $(C_3-C_8)$ cycloalkyl group; (a3) a $(C_3-C_8)$ cycloalkyl $(C_1-C_8)$ alkyl group; (a4) a halo $(C_1-C_8)$ alkyl group; (a5) a $(C_2-C_8)$ alkenyl group; (a6) a $(C_2-C_8)$ alkynyl group; (a7) an aryl group; or (a8) an aryl group having 1 to 5 substituents which may be the same or different and are selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo$(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different;
$R^1$ represents (b1) a $(C_1-C_8)$ alkyl group; (b2) a halo $(C_1-C_8)$ alkyl group; (b3) a $(C_3-C_8)$ cycloalkyl group; (b4) a halo $(C_3-C_8)$ cycloalkyl group; (b5) a $(C_3-C_8)$ cycloalkyl $(C_1-C_8)$ alkyl group; (b6) a halo $(C_3-C_8)$ cycloalkyl $(C_1-C_8)$ alkyl group; (b7) a $(C_2-C_8)$ alkenyl group; (b8) a halo$(C_2-C_8)$ alkenyl group; (b9) a $(C_2-C_8)$ alkynyl group; (b10) a halo $(C_2-C_8)$ alkynyl group; (b11) an aryl group; (b12) an aryl group having 1 to 5 substituents which may be the same or different and are selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo$(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different; (b13) an aryl $(C_1-C_8)$ alkyl group; (b14) an aryl $(C_1-C_6)$ alkyl group having 1 to 5 substituents which may be the same or different and are selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo$(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, the alkyl group may be the same or different; (b15) an aromatic heterocyclic group; (b16) an aromatic heterocyclic group having 1 to 3 substituents which may be the same or different and are selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different; (b17) a $(C_1-C_8)$ alkoxy $(C_1-C_8)$ alkyl group; (b18) a ($C_1$-$C_8$) alkylthio ($C_1$-$C_8$) alkyl group; (b19) a ($C_1$-$C_8$) alkylsulfinyl ($C_1$-$C_8$) alkyl group; or (b20) a ($C_1$-$C_8$) alkylsulfonyl ($C_1$-$C_8$) alkyl group.

X represents O, S, SO, $SO_2$, or $NR^2$, wherein $R^2$ represents a hydrogen atom, a ($C_1$-$C_6$) alkyl group, a ($C_1$-$C_6$)alkylcarbonyl group, a ($C_1$-$C_6$) alkoxycarbonyl group, a ($C_1$-$C_6$) alkylsulfonyl group, or a halo ($C_1$-$C_6$) alkylsulfonyl group, or $R^2$ may bind to $R^1$ to form, together with the nitrogen atom to which $R^2$ binds, a 5- to 8-membered saturated nitrogen-containing aliphatic heterocycle optionally having 1 to 5 substituents, wherein the substituent is selected from a ($C_1$-$C_6$) alkyl group, a ($C_1$-$C_6$)alkylcarbonyl group, a ($C_1$-$C_6$)alkoxycarbonyl group, a ($C_1$-$C_6$) alkylsulfonyl group, a halo ($C_1$-$C_6$) alkylsulfonyl group, and a ($C_1$-$C_6$) alkylenedioxy group, wherein the two oxy groups of the alkylenedioxy group may bind to the same carbon atom or different carbon atoms of the nitrogen-containing aliphatic heterocycle;

Y may be the same or different and represents (c1) a halogen atom; or (c2) a ($C_1$-$C_8$)alkyl group;

m represents 0, 1, 2, or 3.

Z may be the same or different and represents (d1) a halogen atom; (d2) a ($C_1$-$C_8$) alkyl group; (d3) a ($C_3$-$C_8$) cycloalkyl group; (d4) a ($C_3$-$C_8$) cycloalkyl ($C_1$-$C_8$) alkyl group; (d5) a halo ($C_3$-$C_8$) cycloalkyl ($C_1$-$C_8$) alkyl group; (d6) a halo ($C_1$-$C_8$) alkyl group; (d7) a halo ($C_1$-$C_8$) alkoxy group; (d8) a halo ($C_1$-$C_8$) alkylthio group; (d9) a halo($C_1$-$C_8$)alkylsulfinyl group; or (d10) a halo($C_1$-$C_8$)alkylsulfonyl group; and n represents 0, 1, 2, 3 or 4, or a salt thereof;

[2] the benzimidazole compound according to [1], wherein R represents (a1) a ($C_1$-$C_8$) alkyl group; (a2) a ($C_3$-$C_8$) cycloalkyl group; (a3) a ($C_3$-$C_8$) cycloalkyl ($C_1$-$C_8$) alkyl group; (a4) a halo ($C_1$-$C_8$) alkyl group; (a5) a ($C_2$-$C_8$) alkenyl group; (a6) a ($C_2$-$C_8$) alkynyl group; (a7) an aryl group; or (a8) an aryl group having 1 to 5 substituents which may be the same or different and are selected from (a) a halogen atom, (b) a ($C_1$-$C_6$)alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo($C_1$-$C_6$) alkylsulfinyl group, (j) a ($C_1$-$C_6$) alkylsulfonyl group, and (k) a halo($C_1$-$C_6$)alkylsulfonyl group;

$R^1$ represents (b1) a ($C_1$-$C_8$) alkyl group; (b2) a halo($C_1$-$C_8$) alkyl group; (b3) a ($C_3$-$C_8$) cycloalkyl group; (b4) a halo ($C_3$-$C_8$) cycloalkyl group; (b5) a ($C_3$-$C_8$) cycloalkyl ($C_1$-$C_8$) alkyl group; (b6) a halo ($C_3$-$C_8$) cycloalkyl ($C_1$-$C_8$) alkyl group; (b7) a ($C_2$-$C_8$) alkenyl group; (b8) a halo($C_2$-$C_8$) alkenyl group; (b9) a ($C_2$-$C_8$) alkynyl group; (b10) a halo ($C_2$-$C_8$) alkynyl group; (b11) an aryl group; (b12) an aryl group having 1 to 5 substituents which may be the same or different and are selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group; (b13) an aryl ($C_1$-$C_8$) alkyl group; (b14) an aryl($C_1$-$C_6$)alkyl group having 1 to 5 substituents which may be the same or different and are selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group; (b15) an aromatic heterocyclic group; or (b16) an aromatic heterocyclic group having 1 to 3 substituents which may be the same or different and are selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

X represents O, S, SO, $SO_2$, or $NR^2$, wherein $R^2$ represents a hydrogen atom, a ($C_1$-$C_6$) alkyl group, a ($C_1$-$C_6$)alkylcarbonyl group, a ($C_1$-$C_6$) alkoxycarbonyl group, a ($C_1$-$C_6$) alkylsulfonyl group; or a halo ($C_1$-$C_6$) alkylsulfonyl group), Y may be the same or different and represents (c1) a halogen atom; or (c2) a ($C_1$-$C_8$)alkyl group;

m represents 0, 1, 2, or 3;

Z may be the same or different and represents (d1) a halogen atom; (d2) a ($C_1$-$C_8$) alkyl group; (d3) a ($C_3$-$C_8$) cycloalkyl group; (d4) a ($C_3$-$C_8$) cycloalkyl ($C_1$-$C_8$) alkyl group; (d5) a halo ($C_3$-$C_8$) cycloalkyl ($C_1$-$C_8$) alkyl group; (d6) a halo ($C_1$-$C_8$) alkyl group; (d7) a halo ($C_1$-$C_8$) alkoxy group; (d8) a halo ($C_1$-$C_8$) alkylthio group; (d9) a halo($C_1$-$C_8$)alkylsulfinyl group; or (d10) a halo($C_1$-$C_8$)alkylsulfonyl group; and n represents 0, 1, 2, 3, or 4; or a salt thereof;

[3] the benzimidazole compound according to [1], wherein R represents (a1) a ($C_1$-$C_8$) alkyl group; (a2) a ($C_3$-$C_8$) cycloalkyl group; (a4) a halo($C_1$-$C_8$)alkyl group; (a7) an aryl group; or (a8) an aryl group having 1 to 5 substituents which may be the same or different and are selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo($C_1$-$C_6$) alkylsulfinyl group, (j) a ($C_1$-$C_6$) alkylsulfonyl group, (k) a halo ($C_1$-$C_6$) alkylsulfonyl group, and (l) a tri ($C_1$-$C_6$)alkylsilyl group, wherein the alkyl groups may be the same or different;

$R^1$ represents (b1) a ($C_1$-$C_8$) alkyl group; (b2) a halo($C_1$-$C_8$) alkyl group; (b3) a ($C_3$-$C_8$) cycloalkyl group; (b5) a ($C_3$-$C_8$) cycloalkyl ($C_1$-$C_8$) alkyl group; (b11) an aryl group; (b12) an aryl group having 1 to 5 substituents which may be the same or different and are selected from (a) a halogen atom, (b) a ($C_1$-$C_6$) alkyl group, (c) a halo($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, (k) a halo ($C_1$-$C_6$) alkylsulfonyl group, and (l) a tri($C_1$-$C_6$)alkylsilyl group, wherein the alkyl groups may be the same or different; (b13) an aryl ($C_1$-$C_8$) alkyl group; (b14) an aryl ($C_1$-$C_6$) alkyl group having 1 to 5 substituents which may be the same or different and are selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo($C_1$-$C_6$) alkylsulfinyl group, (j) a ($C_1$-$C_6$) alkylsulfonyl group, (k) a halo ($C_1$-$C_6$) alkylsulfonyl group, and (l) a tri ($C_1$-$C_6$)alkylsilyl group, wherein the alkyl groups may be the same or different; (b17) a ($C_1$-$C_8$) alkoxy ($C_1$-$C_8$) alkyl group; (b18) a ($C_1$-$C_8$) alkylthio ($C_1$-$C_8$) alkyl group; or (b20) a ($C_1$-$C_8$) alkylsulfonyl ($C_1$-$C_8$) alkyl group, X represents O, S, SO, $SO_2$, or $NR^2$, wherein $R^2$ represents a ($C_1$-$C_6$) alkyl group, a ($C_1$-$C_6$) alkylcarbonyl group, or a ($C_1$-$C_6$) alkylsulfonyl group, or $R^2$ may bind to $R^1$ to form, together with the nitrogen atom to which $R^2$ binds, a 5- to 8-membered saturated nitrogen-containing aliphatic heterocycle optionally having 1 to 5 substituents, wherein the substituent is selected from a ($C_1$-$C_6$) alkyl group, a ($C_1$-$C_6$)alkylcarbonyl group, a ($C_1$-$C_6$) alkoxycarbonyl group, a ($C_1$-$C_6$) alkylsulfonyl group, a halo ($C_1$-$C_6$) alkylsulfonyl group, and a ($C_1$-$C_6$) alkylenedioxy group, wherein the two oxy groups of the alkylenedioxy group may bind to the same carbon atom or different carbon atoms of the nitrogen-containing aliphatic heterocycle;

Y may be the same or different and represents (c1) a halogen atom;

m represents 0 or 1;

Z may be the same or different and represents (d1) a halogen atom; or (d2) a ($C_1$-$C_8$)alkyl group; and n represents 0, 1, or 2; or a salt thereof;

[4] the benzimidazole compound according to [1], wherein R represents (a1) a ($C_1$-$C_8$) alkyl group; $R^1$ represents (b1) a halo($C_1$-$C_8$)alkyl group; m represents 0, and n represents 0; or a salt thereof;

[5] an agricultural and horticultural insecticidal and acaricidal agent, comprising the benzimidazole compound or a salt thereof according to any of [1] to [4] as an active ingredient;

[6] a method for using an agricultural and horticultural insecticidal and acaricidal agent, comprising applying an effective amount of the benzimidazole compound or a salt thereof according to any of [1] to [4] to plants or soil;

[7] an ectoparasite control agent for animals, comprising an effective amount of the benzimidazole compound or a salt thereof according to any of [1] to [4] as an active ingredient;

[8] an endoparasite control agent for animals, comprising an effective amount of the benzimidazole compound or a salt thereof according to any of [1] to [4] as an active ingredient.

Advantageous Effects of Invention

The benzimidazole compound wherein a pyridyl group binds at position 2 and a specific N-sulfonyl group is present at position 1 of the present invention or a salt thereof has not only a good effect as an agricultural and horticultural insecticidal and acaricidal agent but also has an effect on pests parasitic in companion animals such as dogs and cats or domestic animals such as cows and sheep.

DESCRIPTION OF EMBODIMENTS

In the definition of the general formula (1) representing the benzimidazole compound wherein a pyridyl group binds at position 2 and a specific N-sulfonyl group is present at position 1 of the present invention or a salt thereof, the term "halo" means "a halogen atom" and refers to a fluorine atom, a chlorine atom, a bromine atom, or an iodine atom.

The term "($C_1$-$C_8$)alkyl group" refers to linear or branched alkyl groups having 1 to 8 carbon atoms such as a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a 2-methylbutyl group, a normal hexyl group, an isohexyl group, a 2-hexyl group, a 3-hexyl group, a 2-methylpentyl group, a 3-methylpentyl group, a 1,1,2-trimethylpropyl group, a 3,3-dimethylbutyl group, a normal heptyl group, a 2-heptyl group, a 3-heptyl group, a 2-methylhexyl group, a 3-methylhexyl group, a 4-methylhexyl group, an isoheptyl group, and a normal octyl group, the term "($C_2$-$C_8$)alkenyl group" refers to linear or branched alkenyl groups having 2 to 8 carbon atoms such as a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group, a heptenyl group, and an octenyl group, and the term "($C_2$-$C_8$)alkynyl group" refers to linear or branched alkynyl groups having 2 to 8 carbon atoms such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group, a heptynyl group, and an octynyl group.

The term "($C_1$-$C_6$)alkyl group" refers to linear or branched alkyl groups having 1 to 6 carbon atoms such as a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a 2-methylbutyl group, a normal hexyl group, an isohexyl group, a 2-hexyl group, a 3-hexyl group, a 2-methylpentyl group, a 3-methylpentyl group, a 1,1,2-trimethylpropyl group, and a 3,3-dimethylbutyl group, the term "($C_2$-$C_6$)alkenyl group" refers to linear or branched alkenyl groups having 2 to 6 carbon atoms such as a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, and a 3,3-dimethyl-1-butenyl group, and the term "($C_2$-$C_6$)alkynyl group" refers to linear or branched alkynyl groups having 2 to 6 carbon atoms such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, and a 3,3-dimethyl-1-butynyl group.

The term "($C_3$-$C_8$)cycloalkyl group" refers to cyclic alkyl groups having 3 to 8 carbon atoms such as a cyclopropyl group, a cyclobutyl group, a cyclopentyl group, a cyclohexyl group, a cycloheptyl group, and a cyclooctyl group, and the term "($C_1$-$C_8$)alkoxy group" refers to linear or branched alkoxy groups having 1 to 8 carbon atoms such as a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, a 1,1,2-trimethylpropyloxy group, a normal heptyloxy group, and a normal octyloxy group.

The term "($C_3$-$C_6$)cycloalkyl group" refers to cyclic alkyl groups having 3 to 6 carbon atoms such as a cyclopropyl group, a cyclobutyl group, a cyclopentyl group, and a cyclohexyl group, and the term "($C_1$-$C_6$)alkoxy group" refers to linear or branched alkoxy groups having 1 to 6 carbon atoms such as a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, and a 1,1,2-trimethylpropyloxy group.

The term "$(C_1-C_8)$ alkylthio group" refers to linear or branched alkylthio groups having 1 to 8 carbon atoms such as a methylthio group, an ethylthio group, a normal propylthio group, an isopropylthio group, a normal butylthio group, a secondary butylthio group, a tertiary butylthio group, a normal pentylthio group, an isopentylthio group, a tertiary pentylthio group, a neopentylthio group, a 2,3-dimethylpropylthio group, a 1-ethylpropylthio group, a 1-methylbutylthio group, a normal hexylthio group, an isohexylthio group, a 1,1,2-trimethylpropylthio group, a normal heptylthio group, and a normal octylthio group, the term "$(C_1-C_8)$alkylsulfinyl group" refers to linear or branched alkylsulfinyl groups having 1 to 8 carbon atoms such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, a 1,1,2-trimethylpropylsulfinyl group, a normal heptylsulfinyl group, and a normal octylsulfinyl group, and the term "$(C_1-C_8)$ alkylsulfonyl group" refers to linear or branched alkylsulfonyl groups having 1 to 8 carbon atoms such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, a 1,1,2-trimethylpropylsulfonyl group, a normal heptylsulfonyl group, and a normal octylsulfonyl group.

The term "$(C_1-C_6)$alkylthio group" refers to linear or branched alkylthio groups having 1 to 6 carbon atoms such as a methylthio group, an ethylthio group, a normal propylthio group, an isopropylthio group, a normal butylthio group, a secondary butylthio group, a tertiary butylthio group, a normal pentylthio group, an isopentylthio group, a tertiary pentylthio group, a neopentylthio group, a 2,3-dimethylpropylthio group, a 1-ethylpropylthio group, a 1-methylbutylthio group, a normal hexylthio group, an isohexylthio group, and a 1,1,2-trimethylpropylthio group, the term "$(C_1-C_6)$alkylsulfinyl group" refers to linear or branched alkylsulfinyl groups having 1 to 6 carbon atoms such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, and a 1,1,2-trimethylpropylsulfinyl group, and the term "$(C_1-C_6)$ alkylsulfonyl group" refers to linear or branched alkylsulfonyl groups having 1 to 6 carbon atoms such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, and a 1,1,2-trimethylpropylsulfonyl group.

The above "$(C_1-C_8)$ alkyl group", "$(C_2-C_8)$ alkenyl group", "$(C_2-C_8)$ alkynyl group", "$(C_3-C_8)$ cycloalkyl group", "$(C_1-C_8)$ alkoxy group", "$(C_1-C_8)$ alkylthio group", "$(C_1-C_8)$ alkylsulfinyl group", or "$(C_1-C_8)$ alkylsulfonyl group" may be substituted with one or more halogen atoms at a substitutable position, and when the number of halogen atoms to be used for substitution is two or more, these halogen atoms may be the same or different. Each of the groups substituted with one or more halogens is termed as "halo $(C_1-C_8)$ alkyl group", "halo $(C_2-C_8)$ alkenyl group", "halo $(C_2-C_8)$ alkynyl group", "halo $(C_3-C_8)$ cycloalkyl group", "halo $(C_1-C_8)$ alkoxy group", "halo $(C_1-C_8)$ alkylthio group", "halo$(C_1-C_8)$alkylsulfinyl group", or "halo$(C_1-C_8)$alkylsulfonyl group".

The above "$(C_1-C_6)$ alkyl group", "$(C_2-C_6)$ alkenyl group", "$(C_2-C_6)$ alkynyl group", "$(C_3-C_6)$ cycloalkyl group", "$(C_1-C_6)$ alkoxy group", "$(C_1-C_6)$ alkylthio group", "$(C_1-C_6)$ alkylsulfinyl group", or "$(C_1-C_6)$ alkylsulfonyl group" may be substituted with one or more halogen atoms at a substitutable position, and when the number of halogen atoms to be used for substitution is two or more, these halogen atoms may be the same or different. Each of the groups substituted with one or more halogens is termed as "halo $(C_1-C_6)$ alkyl group", "halo $(C_2-C_6)$ alkenyl group", "halo $(C_2-C_6)$ alkynyl group", "halo $(C_3-C_6)$ cycloalkyl group", "halo $(C_1-C_6)$ alkoxy group", "halo $(C_1-C_6)$ alkylthio group", "halo$(C_1-C_6)$alkylsulfinyl group", or "halo$(C_1-C_6)$alkylsulfonyl group".

The expressions "$(C_1-C_6)$", "$(C_2-C_6)$", "$(C_3-C_6)$", "$(C_1-C_8)$", "$(C_2-C_8)$", "$(C_3-C_8)$" and the like refer to ranges of the number of carbon atoms of various substituents. The above definition is also applicable to a group to which the above substituent is linked and, for example, "a $(C_3-C_8)$ cycloalkyl $(C_1-C_8)$ alkyl group" refers to a linear or branched cycloalkyl group having 3 to 8 carbon atoms binding to a linear or branched alkyl group having 1 to 8 carbon atoms.

The term "aryl group" refers to aromatic hydrocarbon groups having 6 to 10 carbon atoms such as a phenyl group, a 1-naphthyl group, and a 2-naphthyl group.

The term "aromatic heterocyclic group" refers to 5- to 6-membered monocyclic aromatic heterocyclic groups having 1 to 5 heteroatoms such as oxygen atom, nitrogen atom, and sulfur atom such as fryl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, and triazinyl; and 9- to 18-membered aromatic condensed heterocyclic groups having 1 to 5 heteroatoms such as oxygen atom, nitrogen atom, and sulfur atom such as quinolyl, isoquinolyl, quinazolyl, quinoxalyl, benzofuranyl, benzothienyl, benzoxazolyl, benzoisooxazolyl, benzothiazolyl, benzimidazolyl, benzotriazolyl, indolyl, indazolyl, pyrrolopyradinyl, imidazopyridinyl, imidazopyrazinyl, pyrazolopyridinyl, pyrazolothienyl, and pyrazolotriazinyl.

The term "saturated nitrogen-containing aliphatic heterocycle" refers to 5- to 8-membered saturated nitrogen-containing aliphatic heterocycles having at least one (preferably 1 to 2) nitrogen atom and further optionally having 1 to 2 heteroatoms such as oxygen atom and sulfur atom such as pyrrolidine, piperidine, morpholine, and piperazine.

The term "$(C_1-C_6)$alkylcarbonyl group" refers to alkylcarbonyl groups constituted by a linear or branched alkyl group having 1 to 6 carbon atoms and a carbonyl group such as an acetyl group, a propionyl group, a butyryl group, an isobutyryl group, a normal butylcarbonyl group, an isobutylcarbonyl group, a secondary butylcarbonyl group, a tertiary butylcarbonyl group, a normal pentylcarbonyl group, an isopentylcarbonyl group, a tertiary pentylcarbonyl group, a neopentylcarbonyl group, a 2,3-dimethylpropylcarbonyl group, a 1-ethylpropylcarbonyl group, a 1-methylbutylcarbonyl group, a 2-methylbutylcarbonyl group, a normal hexylcarbonyl group, an isohexylcarbonyl group, a 2-hexylcarbonyl group, a 3-hexylcarbonyl group, a 2-methylpentylcarbonyl group, a 3-methylpentylcarbonyl group, a 1,1,2-trimethylpropylcarbonyl group, a 3,3-dimethylbutylcarbonyl group.

The term "$(C_1-C_6)$alkoxycarbonyl group" refers to alkoxycarbonyl groups constituted by a linear or branched alkoxy group having 1 to 6 carbon atoms and a carbonyl group such as a methoxycarbonyl group, an ethoxycarbonyl group, a normal propoxycarbonyl group, an isopropoxycarbonyl group, a normal butoxycarbonyl group, a secondary butoxycarbonyl group, a tertiary butoxycarbonyl group, a normal pentyloxycarbonyl group, an isopentyloxycarbonyl group, a tertiary pentyloxycarbonyl group, a neopentyloxycarbonyl group, a 2,3-dimethylpropyloxycarbonyl group, a 1-ethylpropyloxycarbonyl group, a 1-methylbutyloxycarbonyl group, a normal hexyloxycarbonyl group, an isohexyloxycarbonyl group, and a 1,1,2-trimethylpropyloxycarbonyl group.

The term "tri$(C_1-C_6)$alkylsilyl group" refers to linear or branched trialkylsilyl groups having 1 to 6 carbon atoms such as a trimethylsilyl group, a triethylsilyl group, a tertiary butyldimethylsilyl group, an ethyldimethylsilyl group, an isopropyldimethylsilyl group, and an n-propyldimethylsilyl group. In this case, the three alkyl groups may be the same or different.

Examples of the term "$(C_1-C_6)$alkylenedioxy group" include a methylenedioxy group and an ethylenedioxy group. The two oxy groups of the alkylenedioxy group may bind to the same carbon atom or different carbon atoms of the nitrogen-containing aliphatic heterocycle.

Examples of the salt of the benzimidazole compound represented by the general formula (1) of the present invention include inorganic acid salts such as hydrochlorides, sulfates, nitrates, and phosphates, organic acid salts such as acetates, fumarates, maleates, oxalates, methanesulfonates, benzenesulphonates, and p-toluenesulfonates, and salts with an inorganic or organic base such as a sodium ion, a potassium ion, a calcium ion, and a trimethylammonium.

The benzimidazole compound represented by the general formula (1) of the present invention and a salt thereof may have one asymmetric center in the structural formula, and the present invention encompasses all the optical isomers and mixtures of these isomers at any ratio.

In the benzimidazole compound represented by the general formula (1) of the present invention or a salt thereof, preferably R is (a1) a $(C_1-C_8)$ alkyl group; (a2) a $(C_3-C_8)$ cycloalkyl group; (a4) a halo$(C_1-C_8)$alkyl group; (a7) an aryl group; or (a8) an aryl group having 1 to 5 substituents which may be the same or different and are selected from (a) a halogen atom, (b) a $(C_1-C_6)$ alkyl group, (c) a halo$(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different);

$R^1$ is (b1) a $(C_1-C_8)$ alkyl group; (b2) a halo $(C_1-C_8)$ alkyl group; (b3) a $(C_3-C_8)$ cycloalkyl group; (b5) a $(C_3-C_8)$ cycloalkyl $(C_1-C_8)$ alkyl group; (b11) an aryl group; (b12) an aryl group having 1 to 5 substituents which may be the same or different and are selected from (a) a halogen atom, (b) a $(C_1-C_8)$ alkyl group, (c) a halo$(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different); (b13) an aryl $(C_1-C_8)$ alkyl group; (b14) an aryl $(C_1-C_6)$ alkyl group having 1 to 5 substituents which may be the same or different and are selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo$(C_1-C_6)$ alkylsulfinyl group, (j) a $(C_1-C_6)$ alkylsulfonyl group, (k) a halo $(C_1-C_6)$ alkylsulfonyl group, and (l) a tri$(C_1-C_6)$alkylsilyl group, wherein the alkyl groups may be the same or different); (b17) a $(C_1-C_8)$ alkoxy $(C_1-C_8)$ alkyl group; (b18) a $(C_1-C_8)$ alkylthio $(C_1-C_8)$ alkyl group; or (b20) a $(C_1-C_8)$ alkylsulfonyl $(C_1-C_8)$ alkyl group, X is O, S, SO, $SO_2$, or $NR^2$, wherein $R^2$ represents a $(C_1-C_6)$ alkyl group, a $(C_1-C_6)$ alkylcarbonyl group, or a $(C_1-C_6)$ alkylsulfonyl group. Alternatively, $R^2$ may bind to $R^1$ to form, together with the nitrogen atom to which $R^2$ binds, a 5- to 8-membered saturated nitrogen-containing aliphatic heterocycle optionally having 1 to 5 substituents, wherein the substituent is selected from a $(C_1-C_6)$ alkyl group, a $(C_1-C_6)$ alkylcarbonyl group, a $(C_1-C_6)$ alkoxycarbonyl group, a $(C_1-C_6)$ alkylsulfinyl group, a halo $(C_1-C_6)$ alkylsulfonyl group, and a $(C_1-C_6)$ alkylenedioxy group, wherein the two oxy groups of the alkylenedioxy group may bind to the same carbon atom or different carbon atoms of the nitrogen-containing aliphatic heterocycle))), Y may be the same or different and is (c1) a halogen atom, m is 0 or 1, Z may be the same or different and is (d1) a halogen atom; or (d2) a $(C_1-C_8)$ alkyl group, n is 0, 1, or 2.

Further preferably, R is (a1) a $(C_1-C_6)$ alkyl group, $R^1$ is (b1) a halo$(C_1-C_6)$ alkyl group, and m and n are 0.

The benzimidazole compound represented by the general formula (1) of the present invention or a salt thereof can be produced by, for example, the production method shown below but the present invention is not limited thereto.

Production Method 1

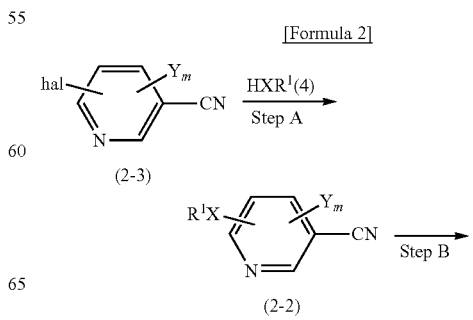

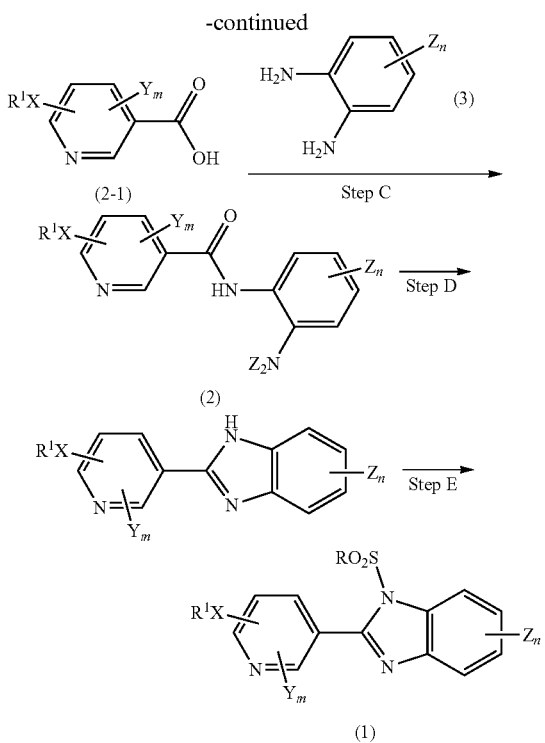

wherein R, $R^1$, X, Y, Z, m and n are the same as above, and hal represents a halogen atom.

Production Method of Step [A]

A nitrile compound represented by general formula (2-2) can be produced by reacting a compound represented by general formula (2-3) and a compound represented by general formula (4) in the presence of a base and an inert solvent.

Examples of the base used in the present reaction include inorganic bases such as sodium hydroxide, potassium hydroxide, sodium carbonate, potassium carbonate, sodium hydrogen carbonate, and potassium hydrogen carbonate, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene, nitrogen-containing aromatic compounds such as pyridine and dimethylaminopyridine, and these bases are used in an amount ranging typically from 1 to 10 times molar amount relative to the compound represented by the general formula (4).

Examples of the inert solvent used in the present reaction can be any solvent as long as it does not notably inhibit progress of the present reaction and examples can include inert solvents such as aromatic hydrocarbons such as benzene, toluene, and xylene, halogenated hydrocarbons such as methylene chloride, chloroform, and carbon tetrachloride; halogenated aromatic hydrocarbons such as chlorobenzene and dichlorobenzene, chain or cyclic ethers such as diethyl ether, methyl tertiary butyl ether, dioxane, and tetrahydrofuran, esters such as ethyl acetate, amides such as dimethylformamide and dimethylacetamide, ketones such as acetone and methyl ethyl ketone, polar solvents such as dimethylsulfoxide, 1,3-dimethyl-2-imidazolidinone, and N-methylpyrrolidone (NMP), and one of these inert solvents may be used alone, or also two or more of them may be used in mixture.

The present reaction is an equimolar reaction and thus each reactant is used in an equal number of moles but any of the reactants can also be overused. The reaction temperature can be in the range from room temperature to a boiling point of an inert solvent to be used, and the reaction time is variable depending on reaction scale and reaction temperature but can be in the range from several minutes to 48 hours.

After completion of the reaction, the desired compound is isolated by a usual method from the reaction system containing the desired compound, and the desired compound can be produced by purification by recrystallization or column chromatography, as needed. Alternatively, the next step may be performed without isolating the intermediate from the reaction system.

Production Method of Step [B]

A carboxylic acid compound represented by general formula (2-1) can be produced by reacting the nitrile compound represented by the general formula (2-2) in the presence of a base and an inert solvent.

Examples of the base used in the present reaction include inorganic bases such as sodium hydroxide, potassium hydroxide, sodium carbonate, potassium carbonate, sodium hydrogen carbonate, and potassium hydrogen carbonate, acetates such as sodium acetate and potassium acetate, and these bases are used in an amount ranging typically from 1 to 10 times the number of moles relative to the compound represented by the general formula (2-2).

Examples of the inert solvent used in the present reaction can be any solvent as long as it does not notably inhibit progress of the present reaction and examples can include inert solvents such as aromatic hydrocarbons such as benzene, toluene, and xylene, halogenated aromatic hydrocarbons such as chlorobenzene and dichlorobenzene, chain or cyclic ethers such as diethyl ether, methyl tertiary butyl ether, dioxane, and tetrahydrofuran, amides such as dimethylformamide and dimethylacetamide, ketones such as acetone and methyl ethyl ketone, polar solvents such as dimethylsulfoxide and 1,3-dimethyl-2-imidazolidinone, alcohols such as methanol, ethanol, propanol, isopropyl alcohol, and water, and one of these inert solvents may be used alone, or also two or more of them may be used in mixture.

After completion of the reaction, the desired compound is isolated by a usual method from the reaction system containing the desired compound, and the desired compound can be produced by purification by recrystallization or column chromatography, as needed.

Production Method of Step [C]

An amide compound represented by general formula (2) can be produced by reacting the carboxylic acid compound represented by the general formula (2-1) and a diamino compound represented by general formula (3) in the presence of a condensing agent, a base, and an inert solvent.

Examples of the condensing agent used in the present reaction can include diethyl phosphorocyanidate (DEPC), carbonyldiimidazole (CDI), 1,3-dicyclohexylcarbodiimide (DCC), 1-ethyl-3-(3-dimethylaminopropyl)carbodiimide (EDC) or a hydrochloride thereof, chlorocarbonic esters, and 2-chloro-1-methylpyridinium iodide, and these agents are used in an application amount appropriately selected from the range from 1 to 1.5 times the number of moles relative to the compound represented by the general formula (2-1).

Examples of the base used in the present reaction include inorganic bases such as sodium hydroxide, potassium hydroxide, sodium carbonate, potassium carbonate, sodium hydrogen carbonate, and potassium hydrogen carbonate, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene, nitrogen-containing aromatic compounds such as pyridine and dimethylaminopyridine (DMAP), and these bases are used in an application amount ranging typically from 0.1 to 10 times the number of moles relative to the compound represented by the general formula (2-1).

Examples of the inert solvent used in the present reaction can be any solvent as long as it does not notably inhibit progress of the present reaction and examples can include inert solvents such as aromatic hydrocarbons such as benzene, toluene, and xylene, halogenated hydrocarbons such as methylene chloride, chloroform, and carbon tetrachloride; halogenated aromatic hydrocarbons such as chlorobenzene and dichlorobenzene, chain or cyclic ethers such as diethyl ether, methyl tertiary butyl ether, dioxane, and tetrahydrofuran, esters such as ethyl acetate, amides such as dimethylformamide and dimethylacetamide, ketones such as acetone and methyl ethyl ketone, polar solvents such as dimethylsulfoxide, 1,3-dimethyl-2-imidazolidinone, and nitrogen-containing aromatic compounds such as pyridine, and one of these inert solvents may be used alone, or also two or more of them may be used in mixture.

The present reaction is an equimolar reaction and thus each reactant is used in an equal number of moles but any of the reactants can also be overused. The reaction temperature can be in the range from room temperature to a boiling point of an inert solvent to be used, and the reaction time is variable depending on reaction scale and reaction temperature but can be in the range from several minutes to 48 hours.

After completion of the reaction, the desired compound is isolated by a usual method from the reaction system containing the desired compound, and the desired compound can be produced by purification by recrystallization or column chromatography, as needed. Alternatively, the next step may be performed without isolating the intermediate from the reaction system.

Production Method of Step [D]

A benzimidazole compound represented by general formula (1-1) can be produced by reacting the amide compound represented by the general formula (2) in the presence of an acid and an inert solvent.

Examples of the acid used in the reaction can include inorganic acids such as a hydrochloric acid, a sulfuric acid, a nitric acid, organic acids such as a formic acid, an acetic acid, a propionic acid, a trifluoroacetic acid, and a benzoic acid, sulfonic acids such as a methanesulfonic acid, a trifluoromethanesulfonic acid, and a para-toluenesulfonic acid, and phosphoric acids, and these acids are used in an application amount appropriately selected from the range from 0.01 to 10 times the number of moles relative to the amide compound represented by the general formula (1-1).

Examples of the inert solvent used in the present reaction can be any solvent as long as it does not notably inhibit progress of the present reaction and examples can include inert solvents such as aromatic hydrocarbons such as benzene, toluene, and xylene, halogenated hydrocarbons such as methylene chloride, chloroform, and carbon tetrachloride; halogenated aromatic hydrocarbons such as chlorobenzene and dichlorobenzene, chain or cyclic ethers such as diethyl ether, methyl tertiary butyl ether, dioxane, and tetrahydrofuran, esters such as ethyl acetate, amides such as dimethylformamide and dimethylacetamide, ketones such as acetone and methyl ethyl ketone, polar solvents such as dimethylsulfoxide, 1,3-dimethyl-2-imidazolidinone, and N-methylpyrrolidone (NMP), and one of these inert solvents may be used alone, or also two or more of them may be used in mixture.

After completion of the reaction, the desired compound is isolated by a usual method from the reaction system containing the desired compound, and the desired compound can be produced by purification by recrystallization or column chromatography, as needed.

Production Method of Step [E]

A benzimidazole compound represented by the general formula (1) can be produced by reacting the benzimidazole compound represented by the general formula (1-1) and a corresponding sulfonyl chloride in the presence of an inert solvent and a base.

Examples of the base used in the present reaction include inorganic bases such as sodium hydroxide, potassium hydroxide, sodium carbonate, potassium carbonate, sodium hydrogen carbonate, potassium hydrogen carbonate, and sodium hydride, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene, nitrogen-containing aromatic compounds such as pyridine and dimethylaminopyridine, and these bases are used in an application amount ranging typically from 1 time to 10 times the number of moles relative to the compound represented by the general formula (1-1).

Examples of the inert solvent used in the present reaction can be any solvent as long as it does not notably inhibit progress of the present reaction and examples can include aromatic hydrocarbons such as benzene, toluene, and xylene, halogenated hydrocarbons such as methylene chloride, chloroform, and carbon tetrachloride; halogenated aromatic hydrocarbons such as chlorobenzene and dichlorobenzene, chain or cyclic ethers such as diethyl ether, tetrahydrofuran (THF), and dioxane, and one of these inert solvents may be used alone, or also two or more of them may be used in mixture.

The sulfonyl chloride used in the present invention is not particularly limited as long as a sulfonyl chloride is represented by a formula: $RSO_2Cl$ (R is the same as described above). The present reaction is an equimolar reaction and thus each reactant is used in an equal number of moles but any of the reactants can also be overused.

The reaction temperature in the present reaction can be typically in the range from about 0° C. to a boiling point of a solvent to be used, and the reaction time is variable but varies depending on reaction scale and reaction temperature but can be appropriately selected from the range from several minutes to 48 hours.

After completion of the reaction, the desired compound is isolated by a usual method, and the desired compound is produced by purification by recrystallization, distillation or column chromatography, as needed.

Hereinafter, specific examples of the compound of the present invention are shown below. In the table below, Me refers to a methyl group, Et refers to an ethyl group, n-Pr refers to a normal propyl group, i-Pr refers to an isopropyl group, n-Bu refers to a normal butyl group, t-Bu refers to a tertiary butyl group, n-Pen refers to a normal pentyl group, n-Hex refers to a normal hexyl group, c-Pr refers to a cyclopropyl group, c-Pen refers to a cyclopentyl group, c-Hex refers to a cyclohexyl group, c-Hep refers to a cycloheptyl group, Ac refers to an acetyl group, pTol refers to a p-tolyl group, Ph refers to a phenyl group, Bn refers to a benzyl group, and TMS refers to a trimethylsilyl group.

Physical property shows melting points (° C.) or H¹-NMR.
H¹-NMR data are shown in Table 8.

[Formula 3]

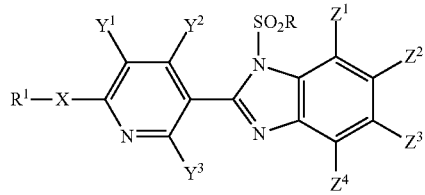

(1a)

TABLE 1

| Compound number | R¹ | X | Y¹ | Y² | Y³ | Z¹ | Z² | Z³ | Z⁴ | R | Physical property |
|---|---|---|---|---|---|---|---|---|---|---|---|
| 1-1 | CF$_3$CH$_2$ | O | H | H | H | H | H | H | H | Et | 99-101 |
| 1-2 | CF$_3$CF$_2$CH$_2$ | O | H | H | H | H | H | H | H | Et | 105-106 |
| 1-3 | CF$_3$CF$_2$CH$_2$ | O | H | H | H | H | H | H | H | Me | 170-172 |
| 1-4 | CF$_3$CF$_2$CH$_2$ | O | H | H | H | H | H | H | H | n-Pr | 89-90 |
| 1-5 | CF$_3$CF$_2$CH$_2$ | O | H | H | H | H | H | H | H | n-Bu | 86-87 |
| 1-6 | CF$_3$CF$_2$CH$_2$ | O | H | H | H | H | H | H | H | c-Pr | 97-98 |
| 1-7 | CF$_3$CF$_2$CH$_2$ | O | H | H | H | H | H | H | H | CF$_3$ | 104-106 |
| 1-8 | CF$_3$CF$_2$CH$_2$ | O | H | H | H | H | H | H | H | pTol | 133-135 |
| 1-9 | CF$_3$CF$_2$CH$_2$ | O | H | H | H | H | H | Br | H | Et | 154-159 |
| 1-10 | CF$_3$CF$_2$CH$_2$ | O | H | H | H | H | Br | H | H | Et | 130-131 |
| 1-11 | CF$_3$CF$_2$CH$_2$ | O | H | H | H | H | H | H | Br | Et |  |
| 1-12 | CF$_3$CF$_2$CH$_2$ | O | H | H | H | H | H | Cl | H | Et | 159-161 |
| 1-13 | CF$_3$CF$_2$CH$_2$ | O | H | H | H | H | Cl | H | H | Et | 119-120 |
| 1-14 | CF$_3$CF$_2$CH$_2$ | O | H | H | H | H | Cl | Cl | H | Et | 177-178 |
| 1-15 | CF$_3$CF$_2$CH$_2$ | O | H | H | H | H | Br | Br | H | Et | 184-186 |
| 1-16 | CF$_3$CF$_2$CH$_2$ | O | H | H | H | H | Br | H | Br | Et |  |
| 1-17 | CF$_3$CF$_2$CH$_2$ | O | H | H | H | H | Me | Me | H | Et | 148-149 |
| 1-18 | CF$_3$CF$_2$CH$_2$ | O | Cl | H | H | H | H | H | H | Et | 88-90 |
| 1-19 | CHF$_2$CF$_2$CH$_2$ | O | H | H | H | H | H | H | H | Et | 77-78 |
| 1-20 | CF$_3$CF$_2$CF$_2$CH$_2$ | O | H | H | H | H | H | H | H | Et | 99-101 |
| 1-21 | CF$_3$CF$_2$CF$_2$CH$_2$ | O | H | H | H | H | H | Br | H | Et | 137-138 |
| 1-22 | CF$_3$CF$_2$CF$_2$CH$_2$ | O | H | H | H | H | Br | H | H | Et | 110-112 |
| 1-23 | (CF$_3$)$_2$CH | O | H | H | H | H | H | H | H | Et | 102-104 |
| 1-24 | CF$_3$CHFCF$_2$CH$_2$ | O | H | H | H | H | H | H | H | Et | 93-94 |
| 1-25 | CF$_3$CH$_2$ | NMe | H | H | H | H | H | H | H | Et |  |

TABLE 2

| Compound number | R¹ | X | Y¹ | Y² | Y³ | Z¹ | Z² | Z³ | Z⁴ | R | Physical property |
|---|---|---|---|---|---|---|---|---|---|---|---|
| 1-26 | CF$_3$CH$_2$ | NAc | H | H | H | H | H | H | H | Et |  |
| 1-27 | CF$_3$CH$_2$ | NSO$_2$Et | H | H | H | H | H | H | H | Et |  |
| 1-28 | CF$_3$CF$_2$CH$_2$ | NMe | H | H | H | H | H | H | H | Et |  |
| 1-29 | CF$_3$CF$_2$CH$_2$ | NAc | H | H | H | H | H | H | H | Et |  |
| 1-30 | CF$_3$CF$_2$CH$_2$ | NSO$_2$Et | H | H | H | H | H | H | H | Et |  |
| 1-31 | CF$_3$ | S | H | H | H | H | H | H | H | Et |  |
| 1-32 | CF$_3$ | SO | H | H | H | H | H | H | H | Et |  |
| 1-33 | CF$_3$ | SO$_2$ | H | H | H | H | H | H | H | Et |  |
| 1-34 | CF$_3$CH$_2$ | S | H | H | H | H | H | H | H | Et |  |
| 1-35 | CF$_3$CH$_2$ | SO | H | H | H | H | H | H | H | Et |  |
| 1-36 | CF$_3$CH$_2$ | SO$_2$ | H | H | H | H | H | H | H | Et |  |
| 1-37 | CF$_3$CF$_2$CH$_2$ | S | H | H | H | H | H | H | H | Et |  |
| 1-38 | CF$_3$CF$_2$CH$_2$ | SO | H | H | H | H | H | H | H | Et |  |
| 1-39 | CF$_3$CF$_2$CH$_2$ | SO$_2$ | H | H | H | H | H | H | H | Et |  |
| 1-40 | 4-CF$_3$SPh | O | H | H | H | H | H | H | H | Et | 135-136 |
| 1-41 | 4-CF$_3$SOPh | O | H | H | H | H | H | H | H | Et | 120-121 |
| 1-42 | 4-CF$_3$SO$_2$Ph | O | H | H | H | H | H | H | H | Et | 122-123 |
| 1-43 | 4-CF$_3$SBn | O | H | H | H | H | H | H | H | Et | 118-119 |
| 1-44 | 4-CF$_3$SOBn | O | H | H | H | H | H | H | H | Et | 110-111 |
| 1-45 | CF$_3$CF$_2$CH$_2$ | O | H | H | H | H | H | H | H | CH$_2$Cl | 113-115 |
| 1-46 | 4-CF$_3$OPh | O | H | H | H | H | H | H | H | Et | 137-138 |
| 1-47 | n-Bu | O | H | H | H | H | H | H | H | Et | 84-85 |

TABLE 2-continued

| Compound number | R$^1$ | X | Y$^1$ | Y$^2$ | Y$^3$ | Z$^1$ | Z$^2$ | Z$^3$ | Z$^4$ | R | Physical property |
|---|---|---|---|---|---|---|---|---|---|---|---|
| 1-48 | n-Pen | O | H | H | H | H | H | H | H | Et | 68-69 |
| 1-49 | n-Hex | O | H | H | H | H | H | H | H | Et | 67-68 |
| 1-50 | c-Pen | O | H | H | H | H | H | H | H | Et | 81-82 |
| 1-51 | c-Hep | O | H | H | H | H | H | H | H | Et | 103-104 |

[Formula 4]

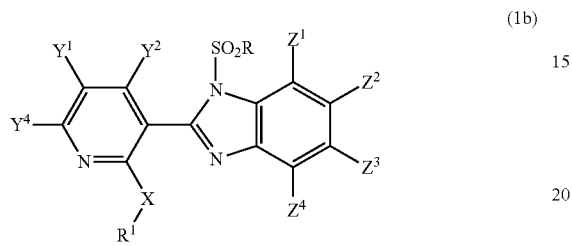

(1b)

TABLE 3

| Compound number | R$^1$ | X | Y$^1$ | Y$^2$ | Y$^4$ | Z$^1$ | Z$^2$ | Z$^3$ | Z$^4$ | R | Physical property |
|---|---|---|---|---|---|---|---|---|---|---|---|
| 2-1 | CF$_3$CF$_2$CH$_2$ | O | H | H | H | H | H | H | H | Et | NMR |

[Formula 5]

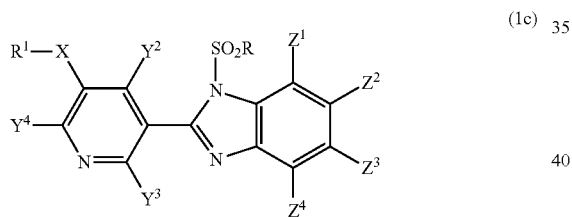

(1c)

TABLE 4

| Compound number | R$^1$ | X | Y$^2$ | Y$^3$ | Y$^4$ | Z$^1$ | Z$^2$ | Z$^3$ | Z$^4$ | R | Physical property |
|---|---|---|---|---|---|---|---|---|---|---|---|
| 3-1 | CF$_3$CF$_2$CH$_2$ | O | H | H | H | H | H | H | H | Et | 93-94 |

[Formula 6]

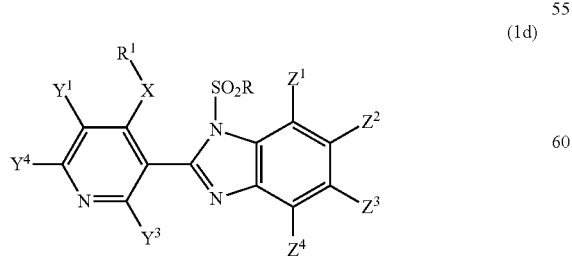

(1d)

TABLE 5

| Compound number | R¹ | X | Y¹ | Y³ | Y⁴ | Z¹ | Z² | Z³ | Z⁴ | R | Physical property |
|---|---|---|---|---|---|---|---|---|---|---|---|
| 4-1 | CF₃CF₂CH₂ | O | H | H | H | H | H | H | H | Et | |

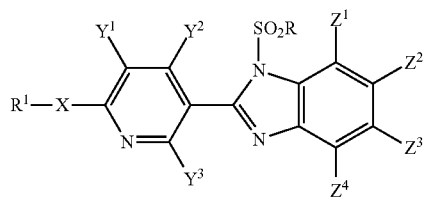

(1a)

TABLE 6

| Compound number | R¹ | X | Y¹ | Physical property |
|---|---|---|---|---|
| 5-1 | n-Pr | O | H | 90-91 |
| 5-2 | i-Pr | O | H | 105-106 |
| 5-3 | c-Hex | O | H | 124-125 |
| 5-4 | t-BuCH₂CH₂ | O | H | 136-137 |
| 5-5 | CH₃OCH₂CH₂ | O | H | 111-112 |
| 5-6 | CH₃SCH₂CH₂ | O | H | 68-69 |
| 5-7 | CH₃SO₂CH₂CH₂ | O | H | 152-153 |
| 5-8 | 4-TMSPh | O | H | 147-149 |
| 5-9 | CF₃CH₂ | O | Cl | 102-105 |
| 5-10 | CHF₂CF₂CH₂ | O | Cl | 98-99 |
| 5-11 | CF₃CF₂CF₂CF₂CF₂CH₂CH₂ | O | H | 86-87 |
| 5-12 | CHF₂CF₂CF₂CF₂CF₂CH₂ | O | H | 77-78 |
| 5-13 | Me | S | H | 137-138 |
| 5-14 | n-Pr | S | H | 110-111 |
| 5-15 | n-Pr | SO | H | 118-119 |
| 5-16 | n-Pr | SO₂ | H | 134-135 |
| 5-17 | n-Bu | S | H | 99-100 |
| 5-18 | c-Pen | S | H | 135-136 |
| 5-19 | c-Hex | S | H | 158-159 |
| 5-20 | c-PrCH₂ | S | H | 125-126 |
| 5-21 | Bn | S | H | 105-106 |
| 5-22 | Bn | SO | H | NMR |
| 5-23 | Bn | SO₂ | H | NMR |
| 5-24 | n-Bu | N(n-Bu) | H | 102-103 |
| 5-25 | n-Bu | NMe | H | NMR |

In formula (1a), R represents an ethyl group, $Y^2$, $Y^3$, $Z^1$, $Z^2$, $Z^3$, and $Z^4$ each represents a hydrogen atom.

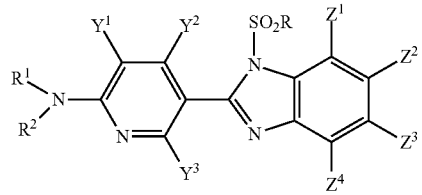

(1a-1)

TABLE 7

| Compound number | N(R¹)R² | Y¹ | Physical property |
|---|---|---|---|
| 6-1 | piperidinyl | H | NMR |
| 6-2 | 1,4-dioxa-8-azaspiro[4.5]decyl | H | NMR |
| 6-3 | ethyl piperidine-4-carboxylate | H | NMR |

In formula (1a-1), R represents an ethyl group, $Y^2$, $Y^3$, $Z^1$, $Z^2$, $Z^3$, and $Z^4$ each represents a hydrogen atom.

TABLE 8

| Compound number | ¹H-NMR Data (CDCl₃) |
|---|---|
| 2-1 | 8.33(dd, 1H), 7.97-7.91(m, 1H), 7.89-7.81(m, 2H), 7.50-7.43(m, 2H), 7.16(dd, 1H), 4.89(br, 2H), 3.32(q, 2H), 1.21(t, 3H) |
| 5-22 | 9.02(m, 1H), 8.13(dd, 1H), 8.01(m, 1H), 7.88(m, 1H), 7.70(dd, 1H), 7.52(m, 2H), 7.25(m, 3H), 4.43(d, 1H), 4.17(d, 1H), 3.17(q, 2H), 1.08(t, 3H) |
| 5-23 | 9.16(m, 1H), 8.20(dd, 1H), 8.01(m, 1H), 7.91(m, 2H), 7.53(m, 2H), 7.28(m, 3H), 7.23(m, 2H), 4.69(s, 2H), 3.22(q, 2H), 1.06(t, 3H) |
| 5-25 | 8.55(d, 1H), 8.00(m, 1H), 7.85(dd, 1H), 7.80(dd, 1H), 7.40(m, 2H), 6.53(d, 1H), 3.58(t, 2H), 3.13(m, 5H), 1.62(m, 2H), 1.37(m, 2H), 1.04(t, 3H), 0.97(t, 3H) |
| 6-1 | 8.56(d, 1H), 7.99(dd, 1H), 7.85(dd, 1H), 7.79(dd, 1H), 7.40(m, 2H), 6.68(d, 1H), 3.66(m, 4H), 3.11(q, 2H), 1.67(m, 5H), 1.51(t, 1H), 1.04(t, 3H) |
| 6-2 | 8.57(m, 1H), 7.99(m, 1H), 7.88(dd, 1H), 7.80(m, 1H), 7.41(m, 2H), 6.72(d, 1H), 4.02(s, 4H), 3.82(t, 4H), 3.12(q, 2H), 1.80(t, 4H), 1.04(t, 3H) |
| 6-3 | 8.57(d, 1H), 8.00(m, 1H), 7.88(dd, 1H), 7.80(m, 1H), 7.42(m, 2H), 6.70(d, 1H), 4.36(m, 2H), 4.16(q, 2H), 3.12(m, 4H), 2.59(m, 1H), 2.01(m, 2H), 1.79(m, 2H), 1.28(t, 3H), 1.04(t, 3H) |

The agricultural and horticultural insecticidal and acaricidal agent comprising the benzimidazole compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, or mites, etc.

Examples of the above pests or nematodes include the following.

Examples of the species of the order Lepidoptera include *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura,* a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina sp., Carposina niponensis, Conogethes punctiferalis, Synanthedon sp., Lyonetia clerkella, Papilio helenus, Colias erate poliographus, Phalera flavescens,* the species of the family Pieridae such as *Pieris rapae* crucivora and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis.*

Examples of the species of the order Hemiptera include *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus spp., Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagons, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wlstarlae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca sp., Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni,*

*Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii.*

Examples of the species of the order Coleoptera include *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Atta* genus unicolor *japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis.*

Examples of the species of the order Diptera include *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella.*

Examples of the species of the order Hymenoptera include *Pristomyrmex pungens,* the species of the family Bethylidae, *Monomorium pharaonis, Pheidole noda, Athalia rosae, Dryocosmus kuriphilus, Formica fusca japonica,* the species of the subfamily Vespinae, *Athalia infumata infumata, Arge pagana, Athalia japonica, Acromyrmex* spp., *Solenopsis* spp., *Arge mali* and *Ochetellus glaber.*

Examples of the species of the order Orthoptera include *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma.*

Examples of the species of the order Thysanoptera include *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdj umovi, Chirothrips manicatus, Frankliniella intonsa, Thrips coloratus, Franklinella occidentalis, Thrips palmi, Frankliniella lilivora* and *Liothrips vaneeckei.*

Examples of the species of the order Acari include *Leptotrombidium akamushi, Tetranychus ludeni, Dermacentor variabilis, Tetranychus truncatus, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.

Examples of the species of the order Isoptera include *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus.*

Examples of the species of the order Blattodea include *Periplaneta fuliginosa, Blattella germanica, Blatta orientalis, Periplaneta brunnea, Blattella lituricollis, Periplaneta japonica* and *Periplaneta americana.*

Examples of the species of the order Siphonaptera include *Pulex irritans, Ctenocephalides felis* and *Ceratophyllus gallinae.*

Examples of the species of the phylum Nematoda include *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans.*

Examples of the species of the phylum Mollusca include such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium Fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

More detailed examples of endoparasites include: the species of the order Enoplida such as *Trichuris* subgenus (whipworms) (*Trichuris* spp.), *Capillaria* subgenus (thread worms) (*Capillaria* spp.), Torikomosoidesu subgenus (*Trichomosoides* spp.), and *Trichinella* subgenus (*Trichinella* genus) (*Trichinella* spp.);

the species of the order Rhabditia such as *Micronema* subgenus (*Micronema* spp.) and *Strongyloides* subgenus (*Strongyloides* spp.);

the species of the order Strongylida, for example, *Stronylus* subgenus (strongyles) (*Stronylus* spp.), *Triodontophorus* subgenus (*Triodontophorus* spp.), *Oesophagodontus* subgenus (*Oesophagodontus* spp.), *Trichonema* subgenus (*Trichonema* spp.), *Gyalocephalus* subgenus (*Gyalocephalus* spp.) *Cylindropharynx* subgenus (*Cylindropharynx* spp.) *Poteriostomum* subgenus (*Poteriostomum* spp.), *Cyclococercus* subgenus (*Cyclococercus* spp.), *Cylicostephanus* subgenus (*Cylicostephanus* spp.), *Oesophagostomum* subgenus (*Oesophagostomum* genus) (*Oesophagostomum* spp.), *Chabertia* subgenus (*Chabertia* spp.), *Stephanurus* subgenus (*Stephanurus dentatus*) (*Stephanurus* spp.), *Ancylostoma* subgenus (old world hookworms) (*Ancylostoma* spp.) *Uncinaria* subgenus (*Uncinaria* spp.), and *Bunostomum* subgenus (*Bunostomum* spp.); *Globocephalus* subgenus (*Globocephalus* spp.), *Syngamus* subgenus (*syngamus* worms) (*Syngamus* spp.), *Cyathostoma* subgenus (*Cyathostoma* spp.), *Metastrongylus* subgenus (lungworms) (*Metastrongylus* spp.), *Dictyocaulus* subgenus (*Dictyocaulus* spp.), *Muellerius* subgenus (*Muellerius* spp.), *Protostrongylus* subgenus (*Protostrongylus* spp.) *Neostrongylus* subgenus (*Neostrongylus* spp.), *Cystocaulus* subgenus (*Cystocaulus* spp.), *Pneumostrongylus* subgenus (*Pneumostrongylus* spp.), *Spicocaulus* subgenus (*Spicocaulus* spp.), *Elaphostrongylus* subgenus (*Elaphostrongylus* spp.), *Parelaphostrongylus* subgenus (*Parelaphostrongylus* spp.) *Crenosoma* subgenus (*Crenosoma* spp.), *Paracrenosoma* subgenus (*Parelaphostrongylus* spp.), *Angiostrongylus* subgenus (*angiostrongylus* worms) (*Angiostrongylus* spp.), *Aelurosutrongylus* subgenus (*Aelurosutrongylus* spp.), *Filaroides* subgenus (*Filaroides* spp.), *Parafilaroides* subgenus (*Parafilaroides* spp.), *Trichostrongylus* subgenus (hairworms) (*Trichostrongylus* spp.), *Haemonchus* subgenus (*haemonchus* worm) (*Haemonchus* spp.), *Ostertagia* subgenus (*Ostertagia* spp.), *Marshallagia* subgenus (*Marshallagia* spp.), *Cooperia* subgenus (*Cooperia* spp.), *Nematodirus* subgenus (nematode) (*Nematodirus* spp.), *Hyostrongylus* subgenus (*Hyostrongylus* spp.), *Obeliscoides* subgenus (*Obeliscoides* spp.), *Amidostomum* subgenus (*Amidostomum* spp.), and *Ollulanus* subgenus (*Ollulanus* spp.);

the species of the order Oxyurida such as *Oxyuris* subgenus (horse pinworms) (*Oxyuris* spp.), *Enterobius* subgenus (pinworms) (*Enterobius* spp.), *Passalurus* subgenus (*Passalurus* spp.), *Syphacia* subgenus (*Syphacia* spp.), *Aspiculuris* subgenus (*Aspiculuris* spp.), and *Heterakis* subgenus (*Heterakis* spp.);

the species of the order Ascaridia such as *Ascaris* subgenus (roundworms) (*Ascaris* spp.), *Toxascaris* subgenus (*Toxascaris* spp.), *Toxocara* subgenus (dog ascariasis) (*Toxocara* spp.), *Parascaris* subgenus (*parascaris equorum*) (*Parascaris* spp.), *Anisakis* subgenus (*Anisakis* spp.), and Ascaridia subgenus (roundworms) (Ascaridia spp.);

the species of the order Spirurida (spiruroids) such as *Gnathostoma* subgenus (*gnathostoma* spinigerm) (*Gnathostoma* spp.), *Physaloptera* subgenus (*Physaloptera* spp.), *Thelazia* subgenus (*Thelazia* spp.), *Gongylonema* subgenus (*Gongylonema* spp.), *Habronema* subgenus (*Habronema* spp.), *Parabronema* subgenus (*Parabronema* spp.), *Draschia* subgenus (*Draschia* spp.), and *Dracunculus* subgenus (Guinea worms) (*Dracunculus* spp.);

the species of the order Filariida such as *Stephanofilaria* subgenus (*Stephanofilaria* spp.), *Parafilaria* subgenus (*Parafilaria* spp.), *Setaria* Subgenus (*Setaria* spp.), *Loa* subgenus (*Loa* spp.), *Dirofilaria* subgenus (dog heartworms) (*Dirofilaria* spp.), *Litomosoides* subgenus (*Litomosoides* spp.), *Brugia* subgenus (*Brugia* spp.), *Wuchereria* subgenus (heartworms) (*Wuchereria* spp.), and *Onchocerca* subgenus (*Onchocerca* spp.); and the species of the order Gigentorhynchida such as *Filicollis* subgenus (*Filicollis* spp.), *Moniliforumis* subgenus (*Moniliforumis* spp.), *Macracanthorhynchus* subgenus (*Macracanthorhynchus* spp.), and *Prosthenorchis* subgenus (*Prosthenorchis* spp.).

The endoparasite control agent comprising the benzimidazole compound represented by the general formula (1) of the present invention or a salt thereof as an active ingredient is effective for not only parasites that live in the body of an intermediate or final host, but also parasites that, live in the body of a reservoir host. The benzimidazole compound represented by the general formula (1) of the present invention or a salt thereof is effective for parasites at their every developmental stage. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound, is effective against their eggs, larvae and adults. The compound of the present invention is capable of not only combating parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection, from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

When the compounds of the present invention are used to control endoparasites in pet mammals and birds, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags. The compounds of the present invention are administered in an arbitrary dosage form suitable for the administration route.

The dosage form may be a solid preparation such as a dust, a granule, a wettable powder, a pellet, a tablet, a ball, a capsule and an molded article containing an active ingredient, a liquid preparation such as an injection fluid, an oral liquid, a liquid preparation applied to the skin or coelom, a pour-on preparation, a spot-on preparation, a flowable, an emulsion, and a semisolid preparation such as an ointment and a gel.

A solid preparation may generally be used by oral administration or by percutaneous or by environmental application after dilution with water or the like. A solid preparation can be prepared by mixing an active ingredient with an appropriate vehicle, and with an adjuvant if necessary, and formulating the mixture into a desired dosage form. Examples of the vehicle include an inorganic vehicle such as a carbonate, a hydrogen carbonate, a phosphate, aluminum oxide, silica or clay or an organic vehicle such as a saccharide, cellulose, cereal flour or starch.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant. Examples of appropriate solvents include water, ethanol, butanol, benzyl alcohol, glycerin, propylene glycol, polyethylene glycol, N-methylpyrrolidone and mixtures thereof, physiologically acceptable vegetable oils and synthetic oils suitable for injection. Examples of solubilizers include polyvinylpyrrolidone, polyoxyethylated castor oil, polyoxyethylated sorbitan ester and the like. Examples of protectants include benzyl alcohol, trichlorobutanol, p-hydroxybenzoic acid esters, n-butanol and the like.

An oral liquid may be administered directly or after dilution and can be prepared in the same manner as an injection fluid.

A flowable, an emulsion or the like may be administered directly or after dilution percutaneously or by environmental application.

A liquid preparation applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added. Examples of appropriate solvents include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone or 2,2-dimethyl-4-oxymethylene-1,3-dioxolane. Examples of absorbefacients include DMSO, isopropyl myristate, pelargonic acid dipropylene glycol, silicone oil, fatty acid esters, triglycerides and aliphatic alcohols. Examples of antioxidants include sulfites, metabisulfites, ascorbic acid, butylhydroxytoluene, butylhydroxyanisole and tocopherol.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickener.

Examples of hydrophobic phases (oils) include paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol and oleyl alcohol.

Examples of hydrophilic phases include water, propylene glycol, glycerin and sorbitol.

Examples of emulsifiers, nonionic surfactants include polyoxyethylated castor oil, polyoxyethylated sorbitan monoolefinic acid, sorbitan monostearate, glycerin monostearate, polyoxyethyl stearate and alkyl phenol polyglycol ether; amphoteric surfactants such as disodium N-lauryl-β-iminodipropionate and lecithin; anionic surfactants such as sodium lauryl sulfate, aliphatic alcohol sulfate ether, mono/dialkylpolyglycol orthophosphate monoethanolamine salt; and cationic surfactants such as cetyltrimethylammonium chloride.

Examples of other additives include carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes and colloidal silica.

A semisolid preparation is administered by applying or spreading onto the skin or introducing into the coelom. A gel can be prepared by adding a thickener to a solution prepared in the same manner as an injection fluid sufficiently to give a transparent viscous substance like an ointment.

In the case where the endoparasite control agent of the present invention is used as a pharmaceutical for animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or divided into multiple doses.

The concentration of the active ingredient in the endoparasite control agent of the present invention is generally about 0.001 to 100% by mass, preferably about 0.001 to 99% by mass, and more preferably about 0.005 to 20% fey mass. The endoparasite control agent of the present invention may be a composition that can be directly administered, or a highly concentrated composition that needs to be diluted to a suitable concentration before use.

The endoparasite control agent of the present Invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural and horticultural insecticidal and acaricidal agent comprising the benzimidazole compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticidal and acaricidal agent is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticidal and acaricidal agent utilizes so-called penetration and translocation. That is, nursery soil, soil in transplanting holes, plant foot, irrigation water, cultivation water in hydroponics, or the like is treated with the agricultural and horticultural insecticidal and acaricidal agent to allow crops, ornamental flowering plants, etc. to absorb the compound of the present invention through the roots via soil or otherwise.

Examples of useful plants to which the agricultural and horticultural insecticidal and acaricidal agent of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticidal and acaricidal agent of the present invention can be applied to these plants as well.

Further, exemplary toxins expressed in genetically modified plants include insecticidal proteins of *Bacillus cereus* or *Bacillus popilliae*; *Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticidal and acaricidal agent of the present invention can be used in combination or used systematically.

In order to control target pests, the agricultural and horticultural insecticidal and acaricidal agent of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticidal and acaricidal agent of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticidal and acaricidal agent of the present invention is commonly used as a formulation convenient for application, which is prepared by the usual method for preparing agrochemical formulations.

That is, the benzimidazole compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticidal and acaricidal agent or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one. Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticidal and acaricidal agent of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticidal and acaricidal agent).

The application rate of the agricultural and horticultural insecticidal and acaricidal agent of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticidal and acaricidal agent of the present invention can be used after mixed with other agricultural and horticultural insecticidal and acaricidal agent, acaricides, nematicides, microbicides, biopesticides and/or the like. Further, the agricultural and horticultural insecticidal and acaricidal agent can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai*, *Bacillus thuringiensis israelensis*, *Bacillus thuringiensis japonensis*, *Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metarn-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, flumeturon, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. Such a combined use of the agricultural and horticultural insecticidal and acaricidal agent of the present invention with the foregoing biopesticide as a mixture can be expected to provide the same effect as above.

Other examples of the biopesticides include natural predators such as *Encarsia Formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLE

Reference Example 1

Production Example of Intermediate (2-2)

Production Method of 5-cyano-2-(2,2,3,3,3-pentafluoropropyloxy)pyridine

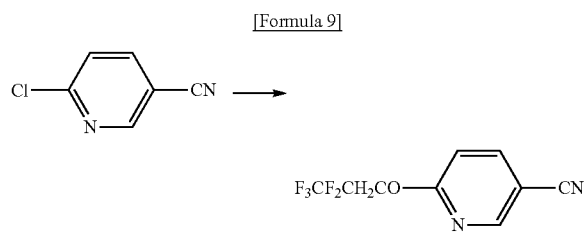

[Formula 9]

2-Chloro-5-cyanopyridine (4.16 g, 30 mmol) was dissolved in NMP (60 mL), 2,2,3,3,3-pentafluoropropanol (6.77 g, 1.5 equivalents) and potassium carbonate (12.4 g, 3.0 equivalents) were added thereto, and then the solution was heated at 100° C. and reacted for 2 hours. After cooling the reaction solution to room temperature, water and ethyl acetate were added to separate the solution, and the organic layer was washed with brine and then dried over sodium sulfate. After distilling off the solvent, purification was performed by column chromatography thereby to obtain the desired compound (7.03 g, yield 93%).

Reference Example 2

Production Method of 6-(2,2,3,3,3-pentafluoropropyloxy)nicotinic Acid

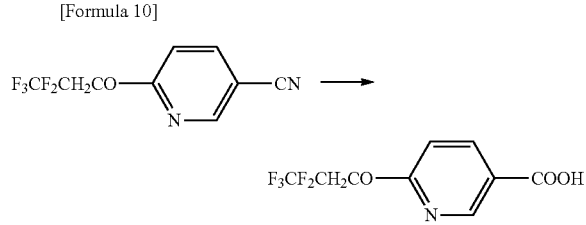

[Formula 10]

The 5-cyano-2-(2,2,3,3,3-pentafluoropropyloxy)pyridine (6.02 g, 24 mmol) obtained in the above step was dissolved in ethanol and water (30 mL) and sodium hydroxide (9.60 g, 10 equivalents) were added thereto, and the solution was refluxed for 2 hours. After cooling the solution to room temperature, a 10% hydrochloric acid solution was added dropwise under the ice bath to neutralize and the extraction was performed with ethyl acetate. The organic layer was washed with brine and then dried over sodium sulfate. The solvent was distilled off to obtain a mixture mainly containing the desired compound (6.40 g).

Reference Example 3

Production Method of 2-(2-(2,2,3,3,3-pentafluoropropyloxy)pyridin-5-yl)benzimidazole

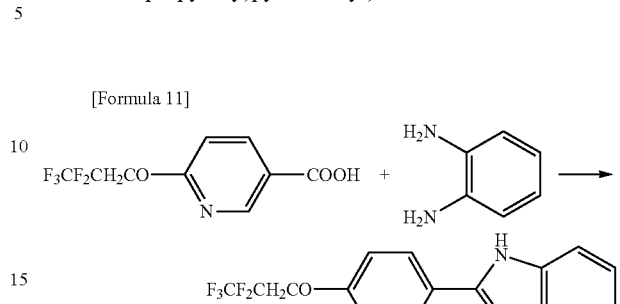

[Formula 11]

6-(2,2,3,3,3-Pentafluoropropyloxy)nicotinic acid (1.47 g, 5.4 mmol) was dissolved in pyridine (10 mL), phenylenediamine (0.70 g, 1.2 equivalents), DMAP (0.13 g, 0.2 equivalents), and EDC.HCl (1.54 g, 1.5 equivalents) were added thereto, and subsequently the solution was reacted for 3 hours at room temperature. Water and ethyl acetate were added to separate the solution and the organic layer was washed sequentially with a 10% hydrochloric acid solution, a potassium carbonate aqueous solution, and brine and dried over sodium sulfate. The solvent was distilled off. The residue was dissolved in NMP (10 mL), a para-toluenesulfonic acid monohydrate (3.08 g, 3 equivalents) was added thereto and subsequently the solution was reacted for 1 hour at 140° C. After cooling the solution to room temperature, a potassium carbonate aqueous solution and ethyl acetate were added to separate the solution. The organic layer was washed with brine and dried over sodium sulfate. After distilling off the solvent, purification was performed by column chromatography thereby to obtain the desired compound (0.67 g, yield 36% (from the previous step)).

Production Example 1

Production Method of 2-(2-(2,2,3,3,3-pentafluoropropyloxy)pyridin-5-yl)-1-ethanesulfonyl benzimidazole (Compound Number 1-2)

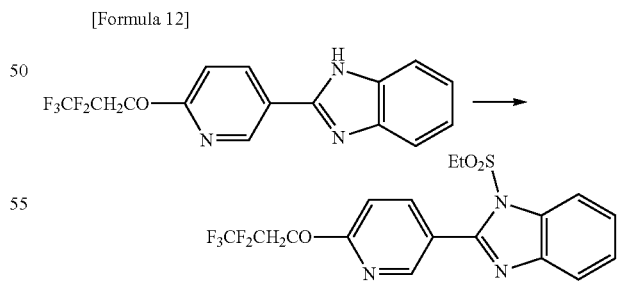

[Formula 12]

2-(2-(2,2,3,3,3-Pentafluoropropyloxy)pyridin-5-yl)benzimidazole (610 mg, 1.8 mmol) obtained in the above step was dissolved in THF (10 mL) and 60% sodium hydroxide (108 mg, 1.5 equivalents) was added at room temperature with stirring. After reacting for 10 minutes, ethanesulfonyl chloride (463 mg, 2.0 equivalents) was added and reacted for 1 hour. Water and ethyl acetate were added sequentially, the organic layer was washed sequentially with a potassium carbonate aqueous solution and brine and dried over sodium sulfate. After distilling off the solvent, the concentrated residue was purified by column chromatography thereby to obtain the desired compound (695 mg, yield 89%).

Hereinafter, formulation examples are shown, but the present invention is not limited thereto. In the formulation examples, "part" means part by weight.

Formulation Example 1

| Compound of the present invention | 10 parts |
|---|---|
| Xylene | 70 parts |
| N-methylpyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| Compound of the present invention | 3 parts |
|---|---|
| Clay powder | 82 parts |
| Diatomite powder | 15 parts |

The above ingredients are uniformly mixed and then pulverized to give a dust formulation.

Formulation Example 3

| Compound of the present invention | 5 parts |
|---|---|
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
|---|---|
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder formulation.

Production Example 5

| Compound of the present invention | 20 parts |
|---|---|
| Polyoxyethylene lauryl ether | 3 parts |
| Sodium dioctyl sulfosuccinate | 3.5 parts |
| Dimethyl sulfoxide | 37 parts |
| 2-Propanol | 36.5 parts |

The above ingredients are uniformly mixed for dissolution to give a water-soluble thickener preparation.

Preparation Example 6

| Compound of the present invention | 2 parts |
|---|---|
| Dimethylsulfoxide | 10 parts |
| 2-Propanol | 35 parts |
| Acetone | 53 parts |

The above ingredients are uniformly mixed for dissolution to give a spray liquid preparation.

Production Example 7

| Compound of the present invention | 5 parts |
|---|---|
| Hexylene glycol | 50 parts |
| Isopropanol | 45 parts |

The above ingredients are uniformly mixed for dissolution to give a liquid preparation for percutaneous administration.

Preparation Example 8

| Compound of the present invention | 5 parts |
|---|---|
| Propylene glycol monomethyl ether | 50 parts |
| Dipropylene glycol | 45 parts |

The above ingredients are uniformly mixed for dissolution to give a liquid preparation for percutaneous administration.

Preparation Example 9

| Compound of the present invention | 2 parts |
|---|---|
| Light liquid paraffin | 98 parts |

The above ingredients are uniformly mixed for dissolution to give a liquid preparation for percutaneous administration (pour-on).

Preparation Example 10

| Compound of the present invention | 2 parts |
|---|---|
| Light liquid paraffin | 58 parts |
| Olive oil | 30 parts |
| ODO-H | 9 parts |
| ShinEtsu Silicone | 1 part |

The above ingredients are uniformly mixed for dissolution to give a liquid preparation for percutaneous administration (pour-on).

Hereinafter, test examples in connection with the present invention are shown, but the present invention is not limited thereto.

Test Example 1

Test for Control Efficacy on Green Peach Aphid (*Myzus persicae*)

Chinese cabbage plants were planted in plastic pots (diameter: 8 cm, height: 8 cm), green peach aphids were propagated on the plants, and the number of surviving Green peach aphids in each pot was counted. The benzimidazole compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

Control rate=100−{(T×Ca)/(Ta×C)}×100 [Expression 1]

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot Criteria
A: the control rate is 100%.
B: the control rate is 90 to 99%.
C: the control rate is 80 to 89%.
D: the control rate is 50 to 79%.

As a result, the compounds 1-3, 1-9, 1-10, 1-20, 1-24, 1-41, 1-42, 5-15, 5-17, and 5-24 of the present invention showed the activity level evaluated as A.

Test Example 2

Insecticidal Test on Small Brown Plant Hopper (*Laodelphax striatellus*)

The benzimidazole compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of small brown plant hopper, and then the glass test tubes were capped with cotton plugs. At 8 days after the inoculation, survival rates were calculated from the numbers of surviving larvae and dead larvae, the corrected mortality rate was calculated according to the formula shown below, and the insecticidal efficacy was evaluated according to the criteria shown below.

Corrected mortality rate (%)=(Survival rate in a non-treatment plot−Survival rate in a treatment plot)/(Survival rate in a non-treatment plot)×100 [Expression 2]

Criteria:
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-7, 1-10, 1-12, 1-13, and 5-15 of the present invention showed the activity level evaluated as A.

Test Example 3

Insecticidal Test on Diamondback Moth (*Plutella xylostella*)

Adults of diamondback moth were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different benzimidazole compound represented by the general formula (1) of the present invention or salt thereof as an active ingredient. After air-dried, the seedlings were kept in a thermostatic chamber at 25° C. At 6 days after the dip treatment, the number of hatched larvae per plot was counted, the corrected mortality rate was calculated according to the formula shown below, and the insecticidal efficacy was evaluated according to the criteria of Test Example 2. This test was conducted in triplicate using 10 adults of diamondback moth per plot.

Corrected mortality rate (%)=(Number of hatched larvae in a non-treatment plot−Number of hatched larvae in a treatment plot)/(Number of hatched larvae in a non-treatment plot)×100 [Expression 3]

As a result, the compounds 1-2, 1-3, 1-4, 1-6, 1-7, 1-9, 1-10, 1-12, 1-13, 1-14, 1-15, 1-17, 1-18, 1-19, 1-20, 1-21, 1-22, 1-23, 1-24, 1-40, 1-41, 1-42, 1-44, 1-45, 3-1, 5-2, 5-10, 5-12, 5-15, 5-18, 5-19, and 5-24 of the present invention showed the activity level evaluated as A.

Test Example 4

Acaricidal Action on Two-Spotted Spider Mite (*Tetranychus urticae*)

Leaf disk having a diameter of 2 cm was prepared by leaves of kidney bean, and the leaf disk was placed on the wetted filter paper. Adult hens of two-spotted spider mite were inoculated on the wetted filter paper, and then 50 ml of an agrochemical dispersion, prepared by diluting a formulation containing the benzimidazole compound represented by the general formula (1) of the present invention or salt thereof as an active ingredient to adjust each of the concentrations to 500 ppm, was sprayed on turntable uniformly. After the spraying, it was allowed to stand in a thermostatic chamber at 25° C. Two days after the treatment of an agrochemical dispersion, the dead mites were counted, the corrected mortality rate was calculated according to the formula shown below, and the acaricidal efficacy was evaluated according to the criteria of Test Example 2. This test was conducted in duplicate using 10 adult hens of two-spotted spider per plot.

Corrected mortality (%)=(Number of dead mites in a non-treatment plot−Number of dead mites in a treatment plot)/(Number of dead mites in a non-treatment plot)×100 [Expression 4]

As a result, the compounds 1-1, 1-2, 1-3, 1-4, 1-5, 1-10, 1-12, 1-13, 1-14, 1-15, 1-17, 1-18, 1-19, 1-20, 1-22, 1-23, 1-24, 1-40, 1-41, 1-42, 1-43, 1-44, 1-45, 1-46, 1-47, 1-48, 1-49, 1-50, 1-51, 3-1, 5-1, 5-2, 5-3, 5-4, 5-5, 5-6, 5-8, 5-9, 5-10, 5-11, 5-12, 5-14, 5-17, 5-18, 5-19, 5-20, 5-21, 5-24, 5-25, and 6-1 of the present invention showed the activity level evaluated as D or higher.

Test Example 5 Impact Evaluation Test on Larvae Motility of *Haemonchus* Nematode (*Haemonchus contortus*)

A DMSO dilute solution of the benzimidazole compound represented by the general formula (1) of the present invention or a salt thereof was put in each well of a 96-well plate containing a predetermined prepared solution to give a final concentration of 50 ppm. Twenty L-1 stage larvae of *Haemonchus* nematode were released and allowed to stand for 4 days, and subsequently the motility ability thereof was investigated. The motility impediment rate of each treatment plot was corrected and calculated based on the impediment efficacy by a DMSO solution alone, and evaluated according to the criteria shown below.

Criteria:
A: the corrected motility impediment rate is 100%
B: the corrected motility impediment rate is 99% to 90%
C: the corrected motility impediment rate is 89% to 80%
D: the corrected motility impediment rate is 79% to 50%

As a result, the compounds 1-9, 1-15, and 1-40 of the present invention showed the activity level evaluated as A.

Test Example 6

Impact Evaluation Test on Larvae Motility of Dog Heartworm (*Dirofilaria immitis*)

Five hundred L-1 stage larvae of dog heartworm diluted in a predetermined prepared solution were inoculated in each well of a 96-well plate, a DMSO dilute solution of the benzimidazole compound represented by the general formula (1) of the present invention or a salt thereof was added to give a final concentration of 50 ppm. Then, the larvae were allowed to stand for 3 days and the mobility ability thereof was investigated. The motility impediment rate of each treatment plot was corrected and calculated based on the impediment efficacy by a DMSO solution alone, and the impact efficacy was evaluated according to the criteria shown below.

Criteria
A: the corrected motility impediment rate is 100%
B: the corrected motility impediment rate is 99% to 90%
C: the corrected motility impediment rate is 89% to 80%
D: the corrected motility impediment rate is 79% to 50%

As a result, the compounds 1-9, 1-15, and 1-40 of the present invention showed the activity level evaluated as A.

INDUSTRIAL APPLICABILITY

The compound of the present invention is highly effective for the control of a wide range of agricultural and horticultural pests and mites and thus is useful.

The invention claimed is:
1. A benzimidazole compound represented by general formula (1)

[Formula 1]

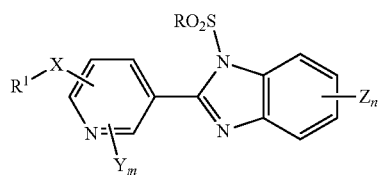

(1)

wherein,
R represents
(a1) a $(C_1-C_8)$alkyl group;
(a2) a $(C_3-C_8)$cycloalkyl group;
(a3) a $(C_3-C_8)$cycloalkyl$(C_1-C_8)$alkyl group;
(a4) a halo$(C_1-C_8)$alkyl group;
(a5) a $(C_2-C_8)$alkenyl group;
(a6) a $(C_2-C_8)$alkynyl group;
(a7) an aryl group; or
(a8) an aryl group having 1 to 5 substituents which may be the same or different and are selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, (k) a halo$(C_1-C_6)$alkylsulfonyl group, and (l) a tri$(C_1-C_6)$alkylsilyl group, wherein the alkyl groups may be the same or different;
$R^1$ represents
(b1) a $(C_1-C_8)$alkyl group;
(b2) a halo$(C_1-C_8)$alkyl group;
(b3) a $(C_3-C_8)$cycloalkyl group;
(b4) a halo$(C_3-C_8)$cycloalkyl group;
(b5) a $(C_3-C_8)$cycloalkyl$(C_1-C_8)$alkyl group;
(b6) a halo$(C_3-C_8)$cycloalkyl$(C_1-C_8)$alkyl group;
(b7) a $(C_2-C_8)$alkenyl group;
(b8) a halo$(C_2-C_8)$alkenyl group;
(b9) a $(C_2-C_8)$alkynyl group;
(b10) a halo$(C_2-C_8)$alkynyl group;
(b11) an aryl group;
(b12) an aryl group having 1 to 5 substituents which may be the same or different and are selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, (k) a halo$(C_1-C_6)$alkylsulfonyl group, and (l) a tri$(C_1-C_6)$alkylsilyl group, wherein the alkyl groups may be the same or different);
(b13) an aryl$(C_1-C_8)$alkyl group:
(b14) an aryl$(C_1-C_8)$alkyl group having 1 to 5 substituents which may be the same or different and are selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, (k) a halo$(C_1-C_6)$alkylsulfonyl group, and (l) a tri$(C_1-C_6)$alkylsilyl group, wherein the alkyl groups may be the same or different;
(b15) an aromatic heterocyclic group;
(b16) an aromatic heterocyclic group having 1 to 3 substituents which may be the same or different and are selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, (f) a $(C_1-C_6)$alkylthio group, (g) a halo$(C_1-C_6)$alkylthio group, (h) a $(C_1-C_6)$alkylsulfinyl group, (i) a halo$(C_1-C_6)$alkylsulfinyl group, (j) a $(C_1-C_6)$alkylsulfonyl group, (k) a halo$(C_1-C_6)$alkylsulfonyl group, and (l) a tri$(C_1-C_6)$alkylsilyl group, wherein the alkyl groups may be the same or different;
(b17) a $(C_1-C_8)$alkoxy$(C_1-C_8)$alkyl group;
(b18) a $(C_1-C_8)$alkylthio$(C_1-C_8)$alkyl group;
(b19) a $(C_1-C_8)$alkylsulfinyl$(C_1-C_8)$alkyl group; or
(b20) a $(C_1-C_8)$alkylsulfonyl$(C_1-C_8)$alkyl group;
X represents O, S, SO, $SO_2$, or $NR^2$, wherein $R^2$ represents a hydrogen atom, a $(C_1-C_6)$alkyl group, a $(C_1-C_6)$alkylcarbonyl group, a $(C_1-C_6)$alkoxycarbonyl group, a $(C_1-C_6)$alkylsulfonyl group, or a halo ($C_1$-$C_6$)alkylsulfonyl group, or $R^2$ may bind to $R^1$ to form, together with the nitrogen atom to which $R^2$ binds, a 5- to 8-membered saturated nitrogen-containing aliphatic heterocycle optionally having 1 to 5 substituents, wherein the substituent is selected from a ($C_1$-$C_6$)alkyl group, a ($C_1$-$C_6$)alkylcarbonyl group, a ($C_1$-$C_6$)alkoxycarbonyl group, a ($C_1$-$C_6$)alkylsulfonyl group, a halo($C_1$-$C_6$)alkylsulfonyl group, and a ($C_1$-$C_6$)alkylenedioxy group, wherein the two oxy groups of the alkylenedioxy group may bind to the same carbon atom or different carbon atoms of the nitrogen-containing aliphatic heterocycle;

Y may be the same or different and represents (c1) a halogen atom; or
(c2) a ($C_1$-$C_8$)alkyl group;
m represents 0, 1, 2, or 3;
Z may be the same or different and represents
(d1) a halogen atom;
(d2) a ($C_1$-$C_8$)alkyl group;
(d3) a ($C_3$-$C_8$)cycloalkyl group;
(d4) a ($C_3$-$C_8$)cycloalkyl($C_1$-$C_8$)alkyl group;
(d5) a halo($C_3$-$C_8$)cycloalkyl($C_1$-$C_8$)alkyl group;
(d6) a halo($C_1$-$C_8$)alkyl group;
(d7) a halo($C_1$-$C_8$)alkoxy group;
(d8) a halo($C_1$-$C_8$)alkylthio group;
(d9) a halo($C_1$-$C_8$)alkylsulfinyl group; or
(d10) a halo($C_1$-$C_8$)alkylsulfonyl group; and
n represents 0, 1, 2, 3 or 4,
or a salt thereof.

2. The benzimidazole compound according to claim 1, wherein

R represents (a1) a ($C_1$-$C_8$)alkyl group;
(a2) a ($C_3$-$C_8$)cycloalkyl group;
(a3) a ($C_3$-$C_8$)cycloalkyl($C_1$-$C_8$)alkyl group;
(a4) a halo($C_1$-$C_8$)alkyl group;
(a5) a ($C_2$-$C_8$)alkenyl group;
(a6) a ($C_2$-$C_8$)alkynyl group;
(a7) an aryl group; or
(a8) an aryl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (l) a tri($C_1$-$C_6$)alkylsilyl group, wherein the alkyl groups may be the same or different;

$R^1$ represents (b1) a ($C_1$-$C_8$)alkyl group;
(b2) a halo($C_1$-$C_8$)alkyl group;
(b3) a ($C_3$-$C_8$)cycloalkyl group;
(b4) a halo($C_3$-$C_8$)cycloalkyl group;
(b5) a ($C_3$-$C_8$)cycloalkyl($C_1$-$C_8$)alkyl group;
(b6) a halo($C_3$-$C_8$)cycloalkyl($C_1$-$C_8$)alkyl group;
(b7) a ($C_2$-$C_8$)alkenyl group;
(b8) a halo($C_2$-$C_8$)alkenyl group;
(b9) a ($C_2$-$C_8$)alkynyl group;
(b10) a halo($C_2$-$C_8$)alkynyl group;
(b11) an aryl group;
(b12) an aryl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (l) a tri($C_1$-$C_6$)alkylsilyl group, wherein the alkyl groups may be the same or different;
(b13) an aryl($C_1$-$C_8$)alkyl group;
(b14) an aryl($C_1$-$C_8$)alkyl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$) alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (l) a tri($C_1$-$C_6$)alkylsilyl group, wherein the alkyl groups may be the same or different;
(b15) an aromatic heterocyclic group; or
(b16) an aromatic heterocyclic group having 1 to 3 substituents which may be the same or different and are selected from (a) a halogen atom, (b) a ($C_1$-$C_6$)alkyl group, (c) a halo($C_1$-$C_6$)alkyl group, (d) a ($C_1$-$C_6$) alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (l) a tri($C_1$-$C_6$)alkylsilyl group, wherein the alkyl groups may be the same or different;

X represents O, S, SO, $SO_2$, or $NR^2$, wherein $R^2$ represents a hydrogen atom, a ($C_1$-$C_6$)alkyl group, a ($C_1$-$C_6$)alkylcarbonyl group, a ($C_1$-$C_6$)alkoxycarbonyl group, a ($C_1$-$C_6$)alkylsulfonyl group; or a halo ($C_1$-$C_6$)alkylsulfonyl group;

Y may be the same or different and represents (c1) a halogen atom; or
(c2) a ($C_1$-$C_8$)alkyl group;
m represents 0, 1, 2, or 3;
Z may be the same or different and represents
(d1) a halogen atom;
(d2) a ($C_1$-$C_8$)alkyl group;
(d3) a ($C_3$-$C_8$)cycloalkyl group;
(d4) a ($C_3$-$C_8$)cycloalkyl($C_1$-$C_8$)alkyl group;
(d5) a halo($C_3$-$C_8$)cycloalkyl($C_1$-$C_8$)alkyl group;
(d6) a halo($C_1$-$C_8$)alkyl group;
(d7) a halo($C_1$-$C_8$)alkoxy group;
(d8) a halo($C_1$-$C_8$)alkylthio group;
(d9) a halo($C_1$-$C_8$)alkylsulfinyl group; or
(d10) a halo($C_1$-$C_8$)alkylsulfonyl group; and
n represents 0, 1, 2, 3, or 4;
or a salt thereof.

3. The benzimidazole compound according to claim 1, wherein

R represents (a1) a ($C_1$-$C_8$)alkyl group;
(a2) a ($C_3$-$C_8$)cycloalkyl group;
(a4) a halo($C_1$-$C_8$)alkyl group;
(a7) an aryl group; or
(a8) an aryl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (1) a tri($C_1$-$C_6$)alkylsilyl group, wherein the alkyl groups may be the same or different;

$R^1$ represents (b1) a ($C_1$-$C_8$)alkyl group;
(b2) a halo($C_1$-$C_8$)alkyl group;
(b3) a ($C_3$-$C_8$)cycloalkyl group;
(b5) a ($C_3$-$C_8$)cycloalkyl($C_1$-$C_8$)alkyl group;
(b11) an aryl group;
(b12) an aryl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (1) a tri($C_1$-$C_6$)alkylsilyl group, wherein the alkyl groups may be the same or different;
(b13) an aryl($C_1$-$C_8$)alkyl group;
(b14) an aryl($C_1$-$C_8$)alkyl group having 1 to 5 substituents which may be the same or different and are selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, (k) a halo($C_1$-$C_6$)alkylsulfonyl group, and (1) a tri($C_1$-$C_6$)alkylsilyl group, wherein the alkyl groups may be the same or different);
(b17) a ($C_1$-$C_8$)alkoxy($C_1$-$C_8$)alkyl group;
(b18) a ($C_1$-$C_8$)alkylthio($C_1$-$C_8$)alkyl group; or
(b20) a ($C_1$-$C_8$)alkylsulfonyl($C_1$-$C_8$)alkyl group, X represents O, S, SO, $SO_2$, or $NR^2$, wherein $R^2$ represents a ($C_1$-$C_6$)alkyl group, a ($C_1$-$C_6$)alkylcarbonyl group, or a ($C_1$-$C_6$)alkylsulfonyl group, or $R^2$ may bind to $R^1$ to form, together with the nitrogen atom to which $R^2$ binds, a 5- to 8-membered saturated nitrogen-containing aliphatic heterocycle optionally having 1 to 5 substituents, wherein the substituent is selected from a ($C_1$-$C_6$)alkyl group, a ($C_1$-$C_6$)alkylcarbonyl group, a ($C_1$-$C_6$)alkoxycarbonyl group, a ($C_1$-$C_6$)alkylsulfonyl group, a halo($C_1$-$C_6$)alkylsulfonyl group, and a ($C_1$-$C_6$)alkylenedioxy group, wherein the two oxy groups of the alkylenedioxy group may bind to the same carbon atom or different carbon atoms of the nitrogen-containing aliphatic heterocycle, Y may be the same or different and represents
(c1) a halogen atom,
  m represents 0 or 1,
Z may be the same or different and represents
(d1) a halogen atom; or
(d2) a ($C_1$-$C_8$)alkyl group, and
  n represents 0, 1, or 2;
or a salt thereof.

4. The benzimidazole compound according to claim 1, wherein

R represents (a1) a ($C_1$-$C_8$)alkyl group;
$R^1$ represents (b1) a halo($C_1$-$C_8$)alkyl group;
m represents 0, and
n represents 0;
or a salt thereof.

5. An agricultural and horticultural insecticidal and acaricidal agent, comprising the benzimidazole compound or a salt thereof according to claim 1 as an active ingredient.

6. A method for using an agricultural and horticultural insecticidal and acaricidal agent, comprising applying an effective amount of the benzimidazole compound or a salt thereof according to claim 1 to plants or soil.

7. An ectoparasite control agent for animals, comprising an effective amount of the benzimidazole compound or a salt thereof according to claim 1 as an active ingredient.

8. An endoparasite control agent for animals, comprising an effective amount of the benzimidazole compound or a salt thereof according to claim 1 as an active ingredient.

9. A method for controlling ectoparasites, comprising orally or parenterally administering, to an animal in need thereof, an effective amount of the benzimidazole compound or a salt thereof according to claim 1 as an active ingredient.

10. A method for controlling endoparasites, comprising orally or parenterally administering, to an animal in need thereof, an effective amount of the benzimidazole compound or a salt thereof according to claim 1 as an active ingredient.

* * * * *